United States Patent
Zhang

(10) Patent No.: US 11,963,740 B2
(45) Date of Patent: Apr. 23, 2024

(54) LUMEN, STENT, AND/OR ARTIFACT DETECTION IN ONE OR MORE IMAGES, SUCH AS IN OPTICAL COHERENCE TOMOGRAPHY IMAGES

(71) Applicant: Canon U.S.A., Inc., Melville, NY (US)

(72) Inventor: Yu Zhang, Concord, MA (US)

(73) Assignee: Canon U.S.A., Inc., Melville, NY (US)

( * ) Notice: Subject to any disclaimer, the term of this patent is extended or adjusted under 35 U.S.C. 154(b) by 253 days.

(21) Appl. No.: 17/098,042

(22) Filed: Nov. 13, 2020

(65) Prior Publication Data
US 2021/0174125 A1 Jun. 10, 2021

Related U.S. Application Data

(60) Provisional application No. 62/944,064, filed on Dec. 5, 2019.

(51) Int. Cl.
*A61B 5/00* (2006.01)
*G06F 18/2431* (2023.01)
(Continued)

(52) U.S. Cl.
CPC .......... *A61B 5/0066* (2013.01); *A61B 5/0071* (2013.01); *A61B 5/0084* (2013.01);
(Continued)

(58) Field of Classification Search
None
See application file for complete search history.

(56) References Cited

U.S. PATENT DOCUMENTS 6,592,549 B2 7/2003 Gerdts et al.
7,872,759 B2 1/2011 Tearney et al.
(Continued)

FOREIGN PATENT DOCUMENTS

JP 2012-505669 A 3/2012
JP 2014-158619 A 9/2014
(Continued)

OTHER PUBLICATIONS

Otsu's Method, From Wikipedia, the free encyclopedia, https://en.wikipedia.org/wiki/Otsu%27s_method, last modified on Oct. 13, 2020.
(Continued)

*Primary Examiner* — Jonathan Cwern
(74) *Attorney, Agent, or Firm* — Canon U.S.A., Inc. I.P. Division

(57) ABSTRACT

One or more devices, systems, methods and storage mediums for performing optical coherence tomography (OCT) while detecting one or more lumen edges, one or more stent struts, and/or one or more artifacts are provided. Examples of applications include imaging, evaluating and diagnosing biological objects, such as, but not limited to, for Gastrointestinal, cardio and/or ophthalmic applications, and being obtained via one or more optical instruments, such as, but not limited to, optical probes, catheters, capsules and needles (e.g., a biopsy needle). Preferably, the OCT devices, systems methods and storage mediums include or involve a method, such as, but not limited to, for removing the detected one or more artifacts from the image(s).

23 Claims, 13 Drawing Sheets

(51) Int. Cl.
*G06T 5/00* (2006.01)
*G06T 7/13* (2017.01)
*G06T 7/73* (2017.01)

(52) U.S. Cl.
CPC ........ *A61B 5/7271* (2013.01); *G06F 18/2431* (2023.01); *G06T 5/005* (2013.01); *G06T 7/13* (2017.01); *G06T 7/73* (2017.01); *A61B 2562/0242* (2013.01); *G06T 2207/10101* (2013.01); *G06T 2207/30021* (2013.01); *G06T 2207/30028* (2013.01); *G06T 2207/30052* (2013.01); *G06T 2207/30101* (2013.01); *G06V 2201/031* (2022.01); *G06V 2201/034* (2022.01)

(56) References Cited

U.S. PATENT DOCUMENTS

| | | | |
|---|---|---|---|
| 7,889,348 B2 | 2/2011 | Tearney et al. | |
| 7,978,916 B2 | 7/2011 | Klingensmith et al. | |
| 8,289,522 B2 | 10/2012 | Tearney et al. | |
| 8,478,387 B2 | 7/2013 | Xu | |
| 8,630,492 B2 | 1/2014 | Klingensmith et al. | |
| 8,913,084 B2 | 12/2014 | Chen et al. | |
| 8,928,889 B2 | 1/2015 | Tearney et al. | |
| 9,138,147 B2 | 9/2015 | Schmitt et al. | |
| 9,173,591 B2 | 11/2015 | Elbasiony et al. | |
| 9,286,673 B2 | 3/2016 | Begin et al. | |
| 9,292,918 B2 | 3/2016 | Zagrodsky et al. | |
| 9,307,926 B2 | 4/2016 | Begin et al. | |
| 9,332,942 B2 | 5/2016 | Jaffer et al. | |
| 9,462,950 B2 | 10/2016 | Xu | |
| 9,852,504 B2 | 12/2017 | Begin et al. | |
| 9,965,891 B2 | 5/2018 | Grady et al. | |
| 9,974,617 B2 | 5/2018 | Flexman et al. | |
| 10,338,795 B2 | 7/2019 | Gopinath et al. | |
| 10,743,749 B2 | 8/2020 | Yamada | |
| 2003/0123698 A1* | 7/2003 | Murakami | H04N 1/3216 |
| | | | 382/280 |
| 2010/0092389 A1 | 4/2010 | Jaffer | |
| 2010/0094127 A1 | 4/2010 | Xu | |
| 2011/0071404 A1 | 3/2011 | Schmitt et al. | |
| 2012/0101374 A1 | 4/2012 | Tearney et al. | |
| 2014/0100440 A1 | 4/2014 | Cheline et al. | |
| 2014/0268167 A1* | 9/2014 | Friedman | G01J 9/02 |
| | | | 356/479 |
| 2016/0213253 A1* | 7/2016 | Wang | A61B 5/14556 |
| 2016/0228097 A1 | 8/2016 | Jaffer et al. | |
| 2017/0140243 A1* | 5/2017 | Ambwani | G06T 7/0014 |
| 2018/0003481 A1 | 1/2018 | Yamada et al. | |
| 2018/0045501 A1 | 2/2018 | Elmaanaoui | |
| 2019/0298174 A1 | 10/2019 | Watanabe | |
| 2019/0374109 A1 | 12/2019 | Wu et al. | |
| 2020/0085285 A1 | 3/2020 | Yamada | |
| 2021/0121132 A1 | 4/2021 | Watanabe et al. | |

FOREIGN PATENT DOCUMENTS

| | | |
|---|---|---|
| JP | 2015-535723 A | 12/2015 |
| WO | 2012/166332 A1 | 12/2012 |
| WO | 2016/047713 A1 | 3/2016 |

OTHER PUBLICATIONS

Hyeong Soo Nam, et al., "Automated detection of vessel lumen and stent struts in intravascular optical coherence tomography to evaluate stent apposition and neointimal coverage", Medical Physics, vol. 43, No. 4, XP012205978, ISSN: 0094-2405, DOI: 10.1118/1.4943374, Mar. 2016, pp. 1662-1675.

* cited by examiner

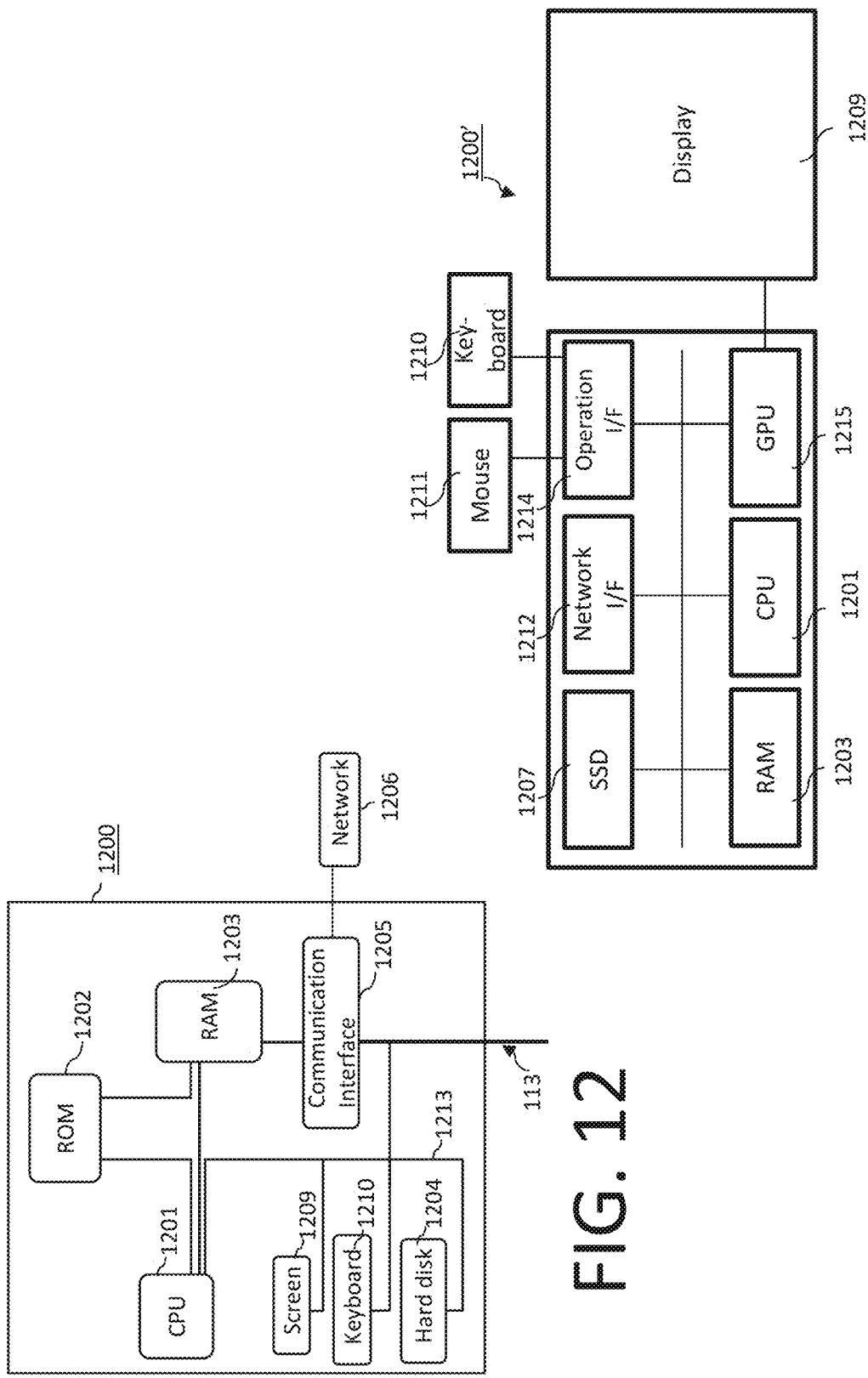

LUMEN, STENT, AND/OR ARTIFACT DETECTION IN ONE OR MORE IMAGES, SUCH AS IN OPTICAL COHERENCE TOMOGRAPHY IMAGES

CROSS-REFERENCE TO RELATED APPLICATION(S)

This application relates, and claims priority, to U.S. Patent Application Ser. No. 62/944,064, filed Dec. 5, 2019, the entire disclosure of which is incorporated by reference herein in its entirety.

FIELD OF THE INVENTION

The present disclosure relates generally to the field of optical imaging and more particularly to one or more optical apparatuses, systems, methods (for using and/or manufacturing) and storage mediums, such as, but not limited to, fiber optic catheters, endoscopes and/or optical coherence tomography (OCT) and/or fluorescence apparatuses and systems, and methods and storage mediums, for use with same, to achieve lumen detection, stent detection, and artifacts detection of images, such as OCT or other (e.g., intravascular ultrasound (IVUS), other lumen image(s), etc.) images. Examples of such applications include imaging, evaluating and diagnosing biological objects, such as, but not limited to, for cardio and/or ophthalmic applications, and being obtained via one or more optical instruments, such as, but not limited to, optical probes, catheters, endoscopes, phase shift units (e.g., galvanometer scanner) and bench top systems.

BACKGROUND OF THE INVENTION

Fiber optic catheters and endoscopes have been developed to access to internal organs. For example in cardiology, OCT has been developed to see depth resolved images of vessels with a catheter. The catheter, which may include a sheath, a coil and an optical probe, may be navigated to a coronary artery.

Optical coherence tomography (OCT) is a technique for obtaining high-resolution cross-sectional images of tissues or materials, and enables real time visualization. The aim of the OCT techniques is to measure the time delay of light by using an interference optical system or interferometry, such as via Fourier Transform or Michelson interferometers. A light from a light source delivers and splits into a reference arm and a sample (or measurement) arm with a splitter (e.g., a beamsplitter). A reference beam is reflected from a reference mirror (partially reflecting or other reflecting element) in the reference arm while a sample beam is reflected or scattered from a sample in the sample arm. Both beams combine (or are recombined) at the splitter and generate interference patterns. The output of the interferometer is detected with one or more detectors, such as, but not limited to, photodiodes or multi-array cameras, in one or more devices, such as, but not limited to, a spectrometer (e.g., a Fourier Transform infrared spectrometer). The interference patterns are generated when the path length of the sample arm matches that of the reference arm to within the coherence length of the light source. By evaluating the output beam, a spectrum of an input radiation may be derived as a function of frequency.

The frequency of the interference patterns corresponds to the distance between the sample arm and the reference arm. The higher frequencies are, the more the path length differences are. Single mode fibers are commonly used for OCT optical probes, and double clad fibers are also commonly used for fluorescence and/or spectroscopy.

In order to obtain geometric measurements of blood vessels from OCT images, lumen edges are detected from the OCT images. Often, image processing approaches for lumen edge detection require more or less uniform illumination of the images such that some optimal global threshold(s) can be determined in order for the image processing algorithms to perform lumen edge detection reliably. To further improve the accuracy of the detected lumen edges, the lumen edge detection results from the neighboring OCT images are correlated to remove outliers and smooth the entire lumen edge.

However, the optimality of global threshold(s) for an image is based on certain assumptions of the underlying image pixel intensity distribution, and images do not always satisfy such assumptions. Therefore, the threshold(s) obtained from the image processing algorithms may not be optimal.

Given the varying curvature and size of the blood vessels, OCT images often display non-uniform illuminations. As such, finding the optimal global threshold(s) tends to be impossible or improbable in image processing algorithms involving pixel intensity and/or gradient based edge detection. For example, in image segmentation based edge detection, optimal global or regional threshold(s) may be applied to intensity values of pixels for an entire image to segment the image into different regions before determining lumen edges from a boundary of the regions. By way of another example, in gradient based edge detection, global threshold(s) may be applied to gradient values of pixels of an image for the entire image and together with gradient directions to detect boundaries where there are significant brightness changes around lumen edges. However, both approaches (i.e., image segmentation and gradient based edge detection) have not considered or addressed uneven illumination, which may affect the lumen edge detection results (e.g., make results inaccurate). Additionally, the segmentation methods are applied on a whole image or on individual A-lines to form a final lumen edge contour. In reality, however, the different geometry positions between lumen and other objects, such as a stent, may lead to confusing or wrong results. In other words, prior approaches focus on optimal image quality and layout conditions without consideration of the complexity of the real world and environmental conditions or other factors that may lead to such confusing or wrong results.

The optimality of global thresholds for an image is based on certain assumptions of the underlying image pixel intensity distribution. It is usually calculated statistically on each image to distinguish between foreground and background. In reality, the images collected suffer from noisy signals, the aforementioned uneven illumination, various artifacts, and the bright metal reflection from the stent and guidewire. The images do not always satisfy such assumptions used for the threshold(s), and therefore the threshold(s) from these algorithms are not always optimal. The overall image quality could play a significant role on the successful identification of the lumen edge points. As at least one example, given the varying curvature and size of blood vessels, OCT images often display non-uniform illuminations. This makes it impossible to find the optimal global thresholds in both pixel intensity and gradient based edge detection algorithms, and, therefore, makes the detection results unreliable using the standard image processing approaches.

Prior approaches for lumen and stent struts detection algorithms using OCT images in general assume ideal image qualities exist, simple lumen shapes are involved, and separated relative positions occur or exist between stents, sheath, guidewire, and lumen. However, in reality, the OCT images could be noisy and non-evenly illuminated. The metal reflection signals generated by guidewire and stent especially when such structures are very close to a light source could be very strong, which either causes an elevation of the signals on the whole A-lines or shows second reflection spots in the shadow area. When lumen edge and stent are very close to each other, a conventional segmentation algorithm may have challenges to distinguish them and select the correct lumen edges. The method of detecting a single edge point on each A-line is not guaranteed to yield the correct lumen edge points all the time, and such a method lacks utilization of checking neighborhood edge point connectivity to avoid outliers or identify special patterns that are not following the normal or preset/predetermined assumption(s). Conventional algorithms also lack or ignore special treatments that may be used to estimate a correct lumen edge, especially in an area where a catheter sheath is attached to a lumen edge and/or where blood residual existed in between or even attached to both the sheath and the vessel wall.

Accordingly, it would be desirable to provide one or more OCT techniques for use in at least one optical device, assembly or system to achieve consistent, reliable detection results at high efficiency and a reasonable cost of manufacture and maintenance.

SUMMARY OF THE INVENTION

Lumen edge detection in OCT imaging may be susceptible to artifacts, which correspond to many features, including, but not limited to: stent strut(s), guide wire(s), image brightness variation due to imaging angle, sheath reflections, an irregular shape of a vessel cross section, etc. Certain applications of OCT, such as multimodality OCT (MMOCT) systems/apparatuses, may use lumen edge detection to correct near-infrared autofluorescence (NIRAF) or near-infrared fluorescence (NIRF) signal distance attenuation. Preferably, accurate, real-time NIRAF or NIRF imaging uses accurate detection of lumen edge(s) in real-time based on a single frame of an OCT image. See, for example, U.S. Pat. Pub. 2019/0298174, U.S. patent application Ser. No. 16/131,662 (which was published on Mar. 19, 2020 as 2020/0085285 and issued as U.S. Pat. No. 10,743,749 on Aug. 18, 2020), and U.S. Pat. Appl. Ser. No. 62/925,655, each of which are herein incorporated by reference in their entireties. Accurately detecting a lumen edge(s) using a single OCT frame helps to improve overall object or target, such as a vessel, measurement accuracy, including for post processing.

In one or more embodiments, a range-based peak search may be applied for each one dimensional (1D) signal (e.g., A-line) of the image in polar coordinate for lumen edge detection and stent strut detection. One or more embodiments may combine pixel intensity values and a separated gradient along A-line values to define a significant edge as the lumen edge, and calculate multiple peak edge pairs for different peak shape(s). One or more embodiments may properly identify a nature of the peaks obtained in a first round by checking neighbor edge point locations (e.g., neighboring the peaks, in neighboring images/A-lines, etc.) and characteristics and grouping such information into separable objects. One or more embodiments may, based on an intensity value, a peak position and peak width values, detect separable objects, and may grow a peak or peaks into respective neighbor A-lines to find local peaks (if available). One or more embodiments may avoid a global shadow profile by using localized calculations for guide wire or stent candidates to examine a shape of a shadow profile and find a center of the stent struts. In one or more embodiments, interpolation of data may be used. For example, one or more embodiments may interpolate missing data or object separation(s) based on correctly identified neighborhood objects with a consideration of A-line transitional effects to improve result(s).

In one or more embodiments of the present disclosure, an OCT image is formed in a polar coordinate system from A-lines. Each A-line includes much information about the imaged object, such as, but not limited to: clear indications of artifacts from metal objects (e.g., stents, stent struts, guide wires, etc.) like narrow signal width and/or sharp rising and falling edges; significant difference in signal intensity and shape for unobstructed soft tissue compared to the sheath reflection and other artifacts like wide signal width and a gentle falling edge. Each A-line represents a cross-sectional 1D sampling of a target, sample, object, etc., such as, but not limited to, a vessel, along a certain view angle. As an imaging probe or device rotates (e.g., rotates about 0 to about 360 degrees, about 180 degrees to about 360 degrees, about 360 degrees, etc.), the corresponding A-lines form the complete two-dimensional (2D) cross-section of the target, sample, object, etc. (e.g., the vessel) in polar coordinates, which is then converted into Cartesian coordinates to form the tomographical-view (tomo-view) image of the cross-section of the target, sample, object, etc. (e.g., the vessel).

In one or more embodiments, individual A-lines may be processed to determine the most significant signal source. A one dimensional (1D) edge location may be determined from each A-line. The types of signal source using the significant difference in an A-line may be determined. Edge points from artifacts may be removed, and gaps may be interpolated. A two dimensional (2D) lumen edge may be formed from the 1D edge result(s). As such, one or more embodiments may have improved processing speed because 1D processing may be faster than corresponding 2D processing.

One or more embodiments may provide more or less uniform, substantially uniform, or uniform illumination of the image(s) such that one or more optical global threshold(s) may be determined to perform lumen edge detection reliably. To further improve the accuracy of the detected lumen edges, the lumen edge detection results from the neighboring OCT images are correlated to remove outliers and smooth the entire lumen edge.

Depending on the vessel curvature, bending, and distance with respect to the imaging probe, some A-lines can have stronger pixel intensity values if the light exiting from imaging probe is close to normal incident to the vessel wall while some other A-lines may have weaker signal when the incidence of the light from the imaging probe to the vessel wall deviates from normal incidence. In addition, when the imaging probe is not located at the center of the vessel, the distance for the light to travel between the probe to the vessel varies as the imaging probe rotates, and produces variation of brightness in one image frame. Therefore, the tomo-view of the vessel may display varying pixel intensity from region to region in one image depending on the corresponding imaging angles and imaging distance to the vessel wall.

Given that an OCT image is formed using an imaging probe spinning inside a vessel in one or more embodiments, the significant edge points or the lumen edge interested may correspond to the inner wall of the imaged vessel. Such a configuration may limit each tomo-view OCT image as having one fully enclosed lumen edge in one or more embodiments. Such a configuration may translate into a situation where there may be only one pixel of interest (such as, but not limited to one lumen edge pixel of interest, one edge pixel of interest, one pixel of interest, a pixel of interest for an edge that is an edge other than a lumen edge, etc.) in each A-line in one or more embodiments. In one or more embodiments, in the presence of stent struts and guidewires, the lumen edge points of the soft tissue may be fully or partially obstructed. Each A line preferably has only one (1) lumen edge pixel or none (when at least one metal artifact presents) in one or more embodiments.

Additionally or alternatively, in one or more embodiments, such a configuration (e.g., an imaging probe spinning inside a vessel, significant edge points or the lumen edge interested corresponding to an inner wall of the imaged vessel, having one fully enclosed lumen edge, etc.) may translate into a process that by confirming a detected major peak edge as a valid lumen edge pixel, multiple peaks presented in a single A-line with different regions of interest may be detectable or detected, and, with a valid connectivity to neighbor objects, the extracted peaks may be joinable or may be joined together and form the objects that are separated in a space.

In one or more embodiments, an initial peak extraction may be obtained on a region of interest in each A-line in a cross-sectional image in a polar coordinate system. By checking a position (e.g., of each A-line, of each edge, of each edge position, etc.) and width parameters' jumps, candidate(s) for external objects, such as guide wire and stents, may be detected beyond the lumen edges. In one or more embodiments, a first step may be to confirm or detect a guide wire region and to remove the guide wire from the lumen edge segments. The removed guide wire may be replaced by the interpolation between neighbor lumen edge pixels. Next, one or more embodiments of the present disclosure may use an iterative approach to process stent candidates one by one to define a correct range or stent region to be use, or for, a shadow profile calculation. The lumen edges may be extracted from the image as much as possible by finding multiple peaks on individual A-line(s) at the border of the different objects. When the shadows from other objects completely block the lumen edge, the lumen edge may be interpolated locally from neighbor lumen edge pixels and represented in a best estimation available from the image. In one or more embodiments, the full curve of the lumen edge may be extracted with all other objects excluded from the results.

One or more lumen, stent, or other object detection technique(s) and/or processes may be used in one or more embodiments of the present disclosure, such as, but not limited to, one or more lumen, stent, or other object detection technique(s) and/or processes as discussed in U.S. patent application Ser. No. 16/414,222, filed on May 16, 2019 and published on Dec. 12, 2019 as U.S. Pat. Pub. No. 2019/0374109, the entire disclosure of which is incorporated by reference herein in its entirety. For example, one or more embodiments of the present disclosure may take advantage of this constraint of having only one lumen edge pixel of interest in each A-line in a cross-sectional image in polar coordinate. By utilizing 1D signal processing techniques to determine this single edge pixel in each A-line, one or more embodiments of the present disclosure simplify the lumen edge detection algorithm and completely eliminate the need of finding global optimal thresholds for the cross-sectional 2D image. This allows each A-line to have its own optimal threshold for best detection result (i.e. total number of A-lines corresponds to number of different thresholds in one image).

By way of another example, one or more embodiments of the present disclosure may further take advantage of a noticeable A-line shape variation due to artifacts from guidewires and stents, and may introduce the falling and rising gradient ratio (FRGR) as a measure of opaqueness and reflectivity to help identify stents struts and other image artifacts from metal during lumen edge detection.

One or more embodiments of the present disclosure of at least one procedure may be described using at least one or more flow diagram. The present disclosure describes one or more features of one or more embodiments of methods in detail, including, but not limited to, about how to detect a lumen edge pixel in an A-line, how to detect an initial lumen edge pixel candidate corresponding peak(s) in an A-line (e.g., using neighborhood connectivity to join peaks into one or more objects), how to identify the edge pixels caused by image artifacts in an OCT image, and how to form the final lumen edge of the imaged vessel.

Further the certain objects such as guide wire and stent struts are identified and confirmed using the shadow profile calculated locally in one or more embodiments. Once each stent shadow is confirmed, its center position is also calculated. Finally, in one or more embodiments, once the whole lumen edge is connected and interpolated for the whole image, the embedded stent struts are also extracted using the same or similar methods, and both the final lumen edge of the imaged vessel and stent strut(s) locations are output (e.g., stored to a memory, shown on a display, printed on a medium (e.g., paper), etc.).

One or more embodiments of the present disclosure model different objects in a 2D image (expandable to 3D) based on their geometry separation by connecting neighbor peaks together, plus using the associated information such as peak value, peak location and peak width to determine the correct object types. The search and growth of the objects may be done locally on a constantly refined region(s) of interest so that the important and relevant information are utilized to generate more reliable or accurate results. The lumen edges presented in the image may be extracted with the proper exclusion of other objects, such as sheath, guide wire, stent, and/or metal reflections. The full connectivity of the complete lumen edge and lumen peak may be ensured by interpolation and smoothening of the results after iteratively removing all stents that cast shadows on the lumen edge in one or more embodiments. Such information allows a further calculation of a better global shadow profile which helps to detect embedded stents more accurately.

Accordingly, it is at least one broad object of the present disclosure to provide one or more optical apparatuses, systems, methods (for using and/or manufacturing) and storage mediums, such as, but not limited to, fiber optic catheters, endoscopes and/or optical coherence tomography (OCT) apparatuses and systems, and methods and storage mediums, for use with same, to achieve consistent, reliable detection results, including at a high efficiency, and at a reasonable cost of manufacture and maintenance.

Two image processing approaches for lumen edge detection are: (i) image segmentation based edge detection where optical global or regional threshold(s) are applied to intensity values of pixels of the OCT images to segment the images into different regions before determining the lumen edges from the boundary of the regions; and (ii) gradient based edge detection where some global threshold(s) are applied to the gradient values of the pixels of the image(s) for the entire image(s) and together with the gradient directions to detect the boundaries where there are significant brightness changes around the lumen edges. In one or more embodiments, cross correlation among neighboring images may be used to improve lumen edge detection results. Results may be used for detection of a device, such as a stent. While these approaches may be used in one or more embodiments, other approaches discussed herein provided advantages over the subject two approaches.

One or more additional objects of the present disclosure are to one or more of: (i) avoid using global threshold(s) in a two-dimensional (2D) image in one or more embodiments; and (ii) combine pixel intensity values and the separated gradient along A-line values and gradient across the A-lines values together for edge detection to improve lumen edge detection accuracy in one or more embodiments. For example, in one or more embodiments of avoiding the use of global threshold(s), 2D image processing may be decoupled into separated 1D signal processing, and an adaptive threshold may be used for each one dimensional (1D) signal (i.e., A-line) of the image in polar coordinate(s) for lumen edge detection.

In one or more embodiments, a one dimensional A-line signal reveals more information about the underlying signal. Lumen edge pixel and artifact pixels may be easily identified using the A-line signal. Preferably, in one or more embodiments, each one dimensional data (A-line) has its own optimal threshold for lumen edge detection. Such feature(s) remove(s) the need of finding global optimal threshold(s) in a 2D image, and reduces the computation complexity. One or more of the subject features also reduce(s) the algorithm sensitivity to regional image intensity variation, and/or provides immunity to intensity variation due to the imaging angle and distance changes.

In one or more embodiments, an optical coherence tomography system for detecting one or more lumen edges, one or more stents, and/or one or more artifacts in one or more images may include: a light source that operates to produce a light; an interference optical system that operates to: (i) receive and divide the light from the light source into a first light with which an object or sample is to be irradiated and a second reference light, (ii) send the second reference light for reflection off of a reference mirror of the interference optical system, and (iii) generate interference light by causing reflected or scattered light of the first light with which the object or sample has been irradiated and the reflected second reference light to combine or recombine, and/or to interfere, with each other, the interference light generating one or more interference patterns; and one or more detectors that operate to continuously acquire the interference light and/or the one or more interference patterns such that the one or more lumen edges, the one or more stents, and/or the one or more artifacts are detected in the images, and the one or more artifacts and/or the one or more stents are removed from the one or more images.

In one or more embodiments, a method for detecting one or more lumen edges, one or more stents, and/or one or more artifacts in at least one image may include: using filtered optical coherence tomography ("OCT") polar coordinate image data to detect one or more of the lumen edges, one or more stents or stent struts, and/or one or more artifacts in the one or more images; detecting and excluding or removing a sheath from the OCT polar coordinate image data; finding a major peak and edge in each one-dimensional (1D) data or A-line of the OCT polar coordinate image data; detecting and removing a guide wire; detecting and processing one or more stent candidates; merging and extending a stent region; calculating a shadow profile and finding or confirming the stent or stent strut and/or a center of the stent or stent strut; extracting a lumen edge near a border of the lumen and the one or more stents or stent struts; interpolating missing data or one or more parts of the lumen edge; finding one or more embedded stents or stent struts; and outputting or storing the lumen edge and stent strut information and/or a location of the center of the stent or stent strut.

One or more method embodiments may include filtering two dimensional (2D) image data to smooth at least one image of a target or object; computing vertical and horizontal gradients of the at least one image; performing one dimensional (1D) filtering to smooth A-line data and gradients in each direction along each A-line; determining or detecting a significant pulse for each A-line, and detecting a lumen edge point in each A-line from the significant pulse; and forming one or more complete lumen edges from the at least one image.

In one or more embodiments, a computer-readable storage medium storing at least one program that operates to cause one or more processors to execute a method for detecting one or more lumen edges, one or more stents, and/or one or more artifacts in at least one image, where the method may include: using filtered optical coherence tomography ("OCT") polar coordinate image data to detect one or more of the lumen edges, one or more stents or stent struts, and/or one or more artifacts in the one or more images; detecting and excluding or removing a sheath from the OCT polar coordinate image data; finding a major peak and edge in each one-dimensional (1D) data or A-line of the OCT polar coordinate image data; detecting and removing a guide wire; detecting and processing one or more stent candidates; merging and extending a stent region; calculating a shadow profile and finding or confirming the stent or stent strut and/or a center of the stent or stent strut; extracting a lumen edge near a border of the lumen and the one or more stents or stent struts; interpolating missing data or one or more parts of the lumen edge; finding one or more embedded stents or stent struts; and outputting or storing the lumen edge and stent strut information and/or a location of the center of the stent or stent strut.

One or more embodiments may include filtering two dimensional (2D) image data to smooth at least one image of a target or object; computing vertical and horizontal gradients of the at least one image; performing one dimensional (1D) filtering to smooth A-line data and gradients in each direction; determining or detecting a significant pulse for each A-line as a lumen edge, or detecting a lumen edge point in each A-line from the significant pulse; and forming one or more complete lumen edges from the at least one image.

In accordance with one or more embodiments of the present disclosure, apparatuses and systems, and methods and storage mediums for lumen, stent, and/or artifacts detection in one or more images may operate to characterize biological objects, such as, but not limited to, blood, mucus, tissue, etc.

It should be noted that one or more embodiments of the lumen, stent, and/or artifact detection method(s) of the present disclosure may be used in other imaging systems, apparatuses or devices, where images are formed from signal reflection and scattering within tissue sample(s) using a scanning probe. For example, IVUS images may be processed in addition to or instead of OCT images.

One or more embodiments of the present disclosure may be used in clinical application(s), such as, but not limited to, intervascular imaging, atherosclerotic plaque assessment, cardiac stent evaluation, balloon sinuplasty, sinus stenting, arthroscopy, ophthalmology, ear research, veterinary use and research, etc.

In accordance with at least another aspect of the present disclosure, one or more technique(s) discussed herein may be employed to reduce the cost of at least one of manufacture and maintenance of the one or more apparatuses, devices, systems and storage mediums by reducing or minimizing a number of optical components and by virtue of the efficient techniques to cut down cost of use/manufacture of such apparatuses, devices, systems and storage mediums.

According to other aspects of the present disclosure, one or more additional devices, one or more systems, one or more methods and one or more storage mediums using, or for use with, one or more lumen edges, stents, and/or artifacts detection techniques are discussed herein. Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein:

FIG. 12 shows a schematic diagram of an embodiment of a computer that may be used with one or more embodiments of at least one apparatus, system, method and/or storage medium, for performing lumen, stent, and/or artifacts detection techniques in accordance with one or more aspects of the present disclosure; and FIG. 13 shows a schematic diagram of another embodiment of a computer that may be used with one or more embodiments of at least one apparatus, system, method and/or storage medium, for performing lumen, stent, and/or artifacts detection techniques in accordance with one or more aspects of the present disclosure.

DETAILED DESCRIPTION OF THE PRESENT INVENTION

One or more devices/apparatuses, optical systems, methods and storage mediums for imaging using lumen, stent, and/or artifacts detection techniques are disclosed herein.

Figure 1:
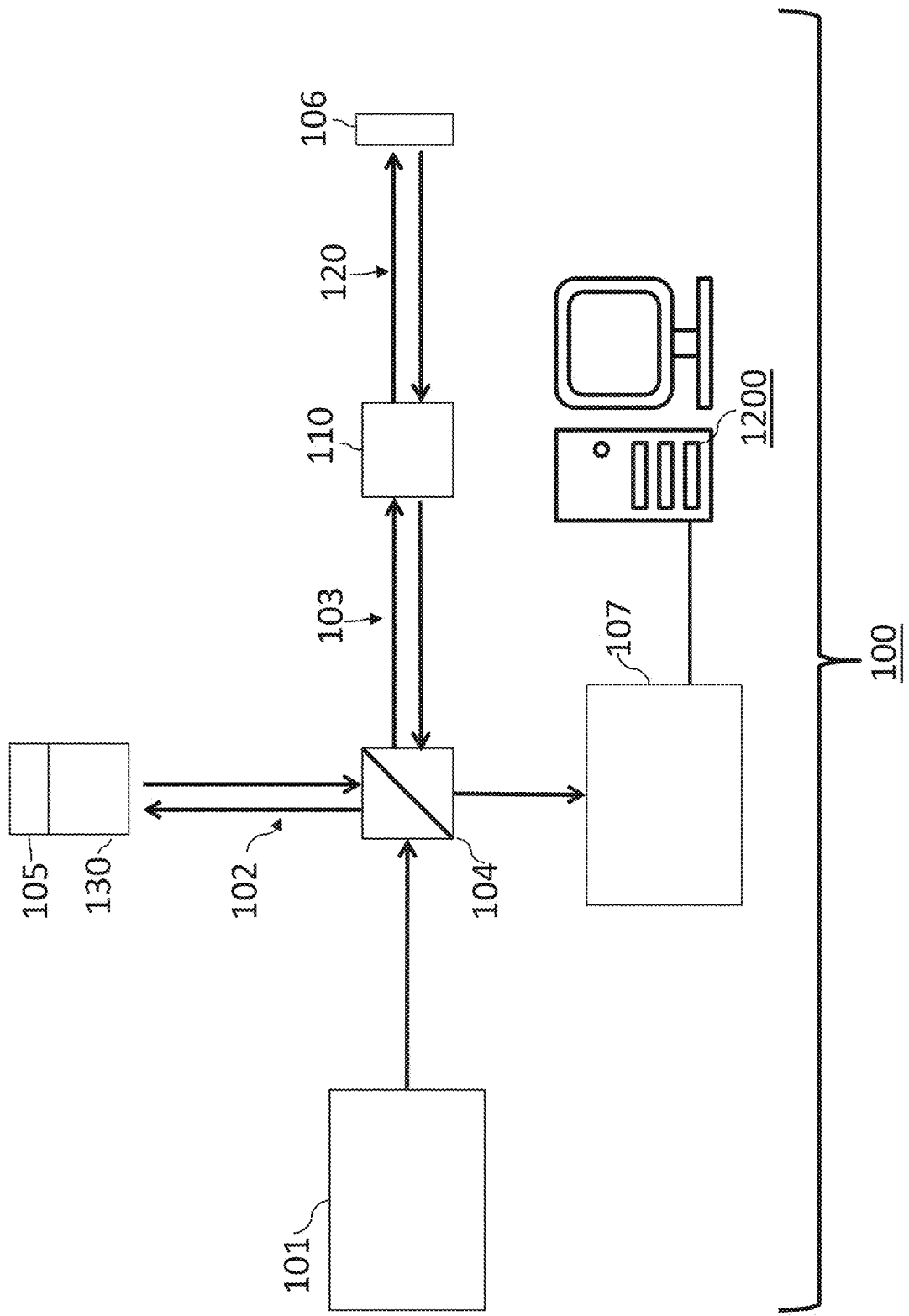
FIG. 1 is a diagram showing an embodiment of a system which can utilize one or more lumen edges, stents, and/or artifacts detection techniques in accordance with one or more aspects of the present disclosure.

Turning now to the details of the figures, FIG. 1 shows an OCT system 100 (as referred to herein as "system 100" or "the system 100") which operates to utilize an OCT technique, including, but not limited to, one or more embodiments of lumen, stent, and/or artifacts detection techniques discussed herein, with optical probe applications in accordance with one or more aspects of the present disclosure. The system 100 comprises a light source 101, a reference arm 102, a sample arm 103, a splitter 104 (also referred to herein as a "beam splitter"), a reference mirror (also referred to herein as a "reference reflection") 105, and one or more detectors 107. The system 100 may include a phase shift device or unit 130, and, in one or more embodiments, the phase shift device or unit may be omitted. In one or more embodiments, the system 100 may include a patient interface device or unit ("PIU") 110 and a catheter 120 (as diagrammatically shown in FIGS. 1-2), and the system 100 may interact with a sample or target 106 (e.g., via the catheter 120 and/or the PIU 110). In one or more embodiments, the system 100 includes an interferometer, or an interferometer is defined by one or more components of the system 100, such as, but not limited to, at least the light source 101, the reference arm 102, the sample arm 103, the splitter 104 and the reference mirror 105.

The light source 101 operates to produce a light to the splitter 104, which splits the light from the light source 101 into a reference beam passing into the reference arm 102 and a sample beam passing into the sample arm 103. The beam splitter 104 is positioned or disposed at an angle to the reference mirror 105, the one or more detectors 107 and to the sample or target 106. The reference beam goes through the phase shift unit 130 (when included in a system, as shown in the system 100), and the reference beam is reflected from the reference mirror 105 in the reference arm 102 while the sample beam is reflected or scattered from a sample 106 through the PIU (patient interface unit) 110 and the catheter 120 in the sample arm 103. Both of the reference and sample beams combine (or recombine) at the splitter 104 and generate interference patterns. The output of the system 100 and/or the interferometer thereof is continuously acquired with the one or more detectors 107, e.g., such as, but not limited to, photodiodes or multi-array cameras. The one or more detectors 107 measure the interference or interference patterns between the two radiation or light beams that are combined or recombined. In one or more embodiments, the reference and sample beams have traveled different optical path lengths such that a fringe effect is created and is measurable by the one or more detectors 107. Electrical analog signals obtained from the output of the system 100 and/or the interferometer thereof are converted to digital signals to be analyzed with a computer, such as, but not limited to, the computer 1200, 1200' (shown in FIG. 12 or FIG. 13, respectively, discussed further below). In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum.

The light source 101 may include a plurality of light sources or may be a single light source. The light source 101 generates broadband laser lights in one or more embodiments. The light source 101 may include one or more of a laser, an organic Light-Emitting Diode (OLED), a Light-Emitting Diode (LED), a halogen lamp, an incandescent lamp, supercontinuum light source pumped by a laser, and/or a fluorescent lamp. The light source 101 may be any light source that provides light which can then be split up into at least three bands in which each band is further dispersed to provide light which is then used to for spectral encoding of spatial information. The light source 101 may be fiber coupled or may be free space coupled to the other components of the system or systems discussed herein, such as, but not limited to, the system 100, the system 100', the system 100'', the system 100''', etc.

In accordance with at least one aspect of the present disclosure, a feature of OCT systems is implemented using fiber optics. As aforementioned, one application of an OCT technique of the present disclosure is to use OCT with a catheter 120 as schematically shown in FIGS. 1-2.

Figure 2:
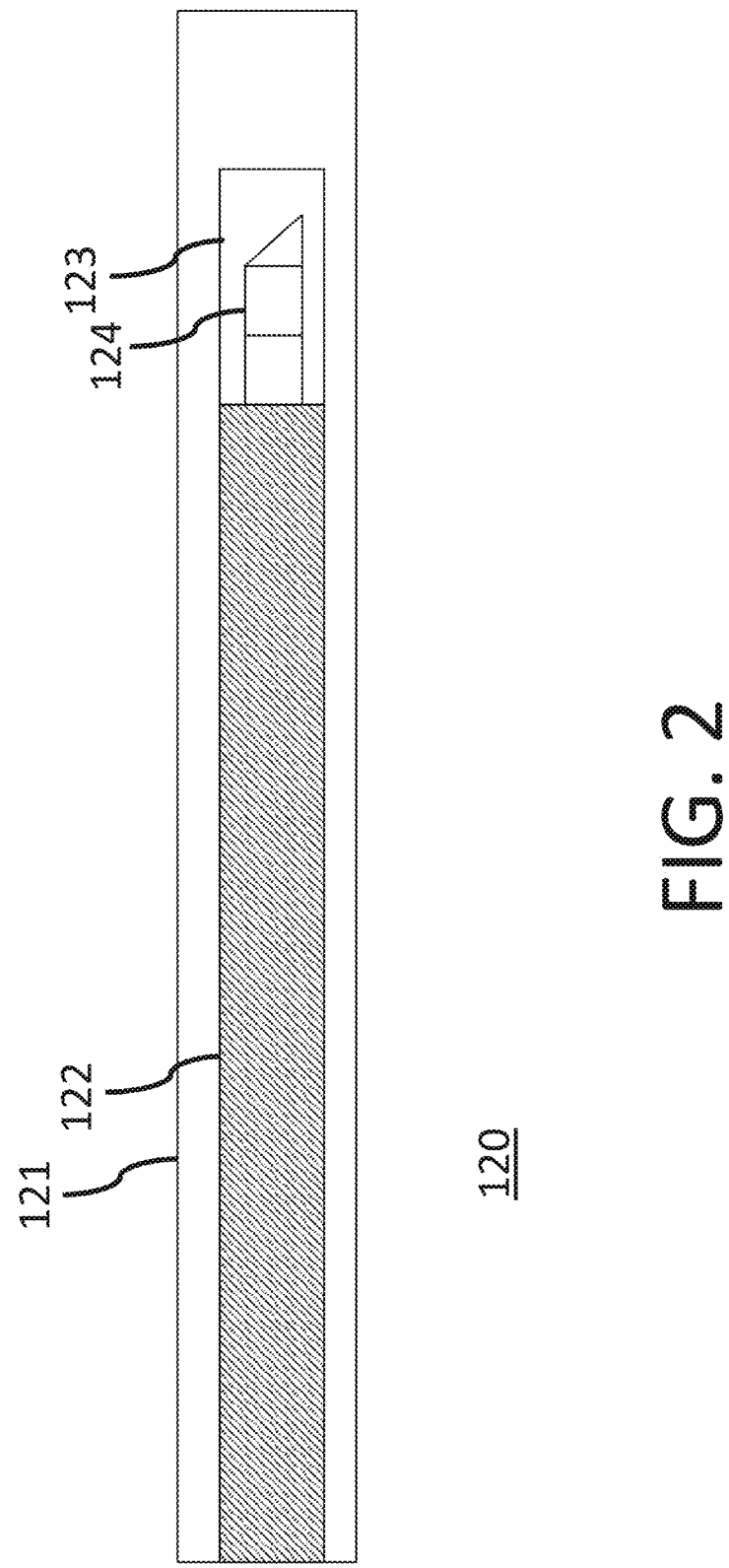
FIG. 2 is a diagram of an embodiment of a catheter that may be used with at least one embodiment of an apparatus or system for performing lumen, stent and/or artifacts detection techniques in accordance with one or more aspects of the present disclosure.

FIG. 2 shows an embodiment of the catheter 120 including a sheath 121, a coil 122, a protector 123 and an optical probe 124. As shown schematically in FIGS. 1-2, the catheter 120 preferably is connected to the PIU no to spin the coil 122 with pullback (e.g., at least one embodiment of the PIU no operates to spin the coil 122 with pullback). The coil 122 delivers torque from a proximal end to a distal end thereof (e.g., via or by a rotational motor in the PIU no). In one or more embodiments, the coil 122 is fixed with/to the optical probe 124 so that a distal tip of the optical probe 124 also spins to see an omnidirectional view of a biological organ, sample or material being evaluated, such as, but not limited to, hollow organs such as vessels, a heart, etc. For example, fiber optic catheters and endoscopes may reside in the sample arm (such as the sample arm 103 as shown in FIG. 1) of an OCT interferometer in order to provide access to internal organs, such as intravascular images, gastro-intestinal tract or any other narrow area, that are difficult to access. As the beam of light through the optical probe 124 inside of the catheter 120 or endoscope is rotated across the surface of interest, cross-sectional images of one or more samples are obtained. In order to acquire three-dimensional data, the optical probe 124 is simultaneously translated longitudinally during the rotational spin resulting in a helical scanning pattern. This translation may be performed by pulling the tip of the probe 124 back towards the proximal end and therefore referred to as a pullback.

In one or more embodiments, the patient user interface no may comprise or include a connection component (or interface module), such as a rotary junction, to connect one or more components, such as one or more components of a probe (e.g., a catheter 120 (see e.g., FIGS. 1-2)), a needle, a capsule, a patient interface unit (e.g., the patient interface unit 110), etc., to one or more other components, such as, an optical component, a light source (e.g., the light source 101), a deflection section (e.g., such as the deflection or deflected section, which is a component that operates to deflect the light from the light source to the interference optical system, and then send light received from the interference optical system towards the at least one detector; a deflection or deflected section that includes at least one of: one or more interferometers, a circulator, a beam splitter, an isolator, a coupler, a fusion fiber coupler, a partially severed mirror with holes therein, and a partially severed mirror with a tap; etc.), the sample arm 102, a motor that operates to power the connection component and/or the patient user interface 110, etc. For example, when the connection member or interface module is a rotary junction, preferably the rotary junction operates as discussed below). In one or more other embodiments, the rotary junction may be at least one of: a contact rotary junction, a lenseless rotary junction, a lens-based rotary junction, or other rotary junction known to those skilled in the art.

In at least one embodiment, the PIU no may include a Fiber Optic Rotary Junction (FORJ), a rotational motor and translation motorized stage (e.g., a portion of the PIU 110), and a catheter connector (e.g., a portion of the PIU 110). The FORJ allows uninterrupted transmission of an optical signal while rotating a fiber along the fiber axis. The FORJ may have a free space optical beam combiner including a rotor and stator.

Descriptions of like-numbered elements present in the system 100' and already described above, such as for the system 100, shall not be repeated, and are incorporated by reference herein in their entireties.

In at least one embodiment, the console 1200, 1200' operates to control motions of a motor and translation motorized stage (hereinafter referred to as "motor" or "motor and stage"), acquires intensity data from the at least one detector(s) 107, and displays the scanned image (e.g., on a monitor or screen such as a display, screen or monitor 1209 as shown in the console 1200 of FIG. 12 and/or the console 1200' of FIG. 13 as further discussed below). In one or more embodiments, the console 1200, 1200' operates to change a speed of the motor and/or to stop the motor. The motor may be a stepping or a DC servo motor to control the speed and increase position accuracy.

In one or more embodiments, the console or computer 1200, 1200' operates to control the system 100 (and other systems, such as, but not limited to, the system 100', the system 100'', the system 100''', etc. as discussed further below), the catheter 120 and/or one or more other above-described components of the system 100. In at least one embodiment, the console or computer 1200, 1200' operates to acquire intensity data from the at least one detector 107 of the OCT system/device/apparatus, and displays the image(s) (e.g., on a monitor or screen such as a display, screen or monitor 1209 as shown in the console 1200 of FIG. 12 and/or the console 1200' of FIG. 13 as further discussed below). The output of the one or more components of the system 100 (and other systems, such as, but not limited to, the system 100', the system 100'', the system 100''', etc. as discussed further below) is acquired with the at least one detector 107 of the OCT system/device/apparatus, e.g., such as, but not limited to, photodiodes, Photomultiplier tube(s) (PMTs), line scan camera(s), or multi-array camera(s). Electrical analog signals obtained from the output of the system 100 (and/or other systems, such as, but not limited to, the system 100', the system 100'', the system 100''', etc. as discussed further below) or one or more components thereof are converted to digital signals to be analyzed with a computer, such as, but not limited to, the computer 1200, 1200' (e.g., as shown in FIGS. 1, 9-11, and 12-13). In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum. In some embodiments, the at least one detector 107 comprises three detectors configured to detect three different bands of light.

In one or more embodiments, a range-based peak search may be applied for each one dimensional (1D) signal (e.g., A-line) of the image in polar coordinate for lumen edge detection and stent strut detection. One or more embodiments may combine pixel intensity values and a separated gradient along A-line values to define a significant edge as the lumen edge, and calculate multiple peak/edge pairs for different peak shape(s). One or more embodiments may properly identify a nature of the peaks obtained in a first round by checking neighbor edge point locations (e.g., neighboring the peaks, in neighboring A-lines, etc.) and characteristics and grouping such information into separable objects. One or more embodiments may, based on intensity values, peak positions and peak widths' values, detect separable objects, and may grow a peak or peaks into neighboring A-lines to find local peaks (if available). One or more embodiments may avoid a global shadow profile by using localized calculations for guide wire or stent candidates to examine a shape of a shadow profile and find a center of the stent struts. In one or more embodiments, interpolation of data may be used. For example, one or more embodiments may interpolate missing data or object separation(s) based on correctly identified neighborhood objects with a consideration of A-line transitional effects to improve result(s).

In one or more embodiments of the present disclosure, an OCT image is formed in a polar coordinate system from A-lines. Each A-line includes much information about the imaged object, such as, but not limited to: clear indications of artifacts from metal objects (e.g., stents, stent struts, guide wires, etc.) like narrow signal width and/or sharp rising and falling edges; significant difference in signal intensity and shape for unobstructed soft tissue compared to the sheath reflection and other artifacts like wide signal width and a gentle falling edge. Each A-line represents a cross-sectional 1D sampling of a target, sample, object, etc., such as, but not limited to, a vessel, along a certain view angle. As an imaging probe or device rotates (e.g., rotates about 0 to about 360 degrees, about 180 degrees to about 360 degrees, about 360 degrees, etc.), the corresponding A-lines form the complete two-dimensional (2D) cross-section of the target, sample, object, etc. (e.g., the vessel) in polar coordinates, which is then converted into Cartesian coordinates to form the tomographical-view (tomo-view) image of the cross-section of the target, sample, object, etc. (e.g., the vessel).

In accordance with at least one aspect of the present disclosure and as aforementioned, one or more methods for lumen, stent, and/or artifacts detection of OCT images are provided herein. For example, one or more method(s) may include one or more of the following: (i) performing OCT image pre-processing (e.g., by preparing a filtered OCT image, a gradient image, and binary images, etc.); (ii) on the filtered OCT image in polar coordinates, finding a sheath edge profile and field of view (FOV) such that the vessel lumen and tissue may be observed; (iii) finding a major peak and the corresponding edges for half-max, maximum gradient and zero gradient on each individual A-line; (iv) detecting a biggest disconnected region in terms of peak value, peak width, or peak location, and confirming it has a valid shadow profile; (v) using the location and the peak width of the major peak to detect a list of stent candidates; (vi) growing the non-lumen peak within the stent candidates to find the correct shadow region until the neighborhood lumen peaks are reached; (vii) calculating the shadow profile on the shadow region locally (and, in one or more embodiments, analyzing the shadow profile shape to confirm the existence of the stent, plus find a center location of the strut); (viii) extracting the lumen peak and edge near the stent shadow and lumen; (ix) performing linear interpolation of the lumen peak and edge behind the shadow; (x) calculating the shadow profile using the complete lumen peak for the whole image (and, if needed in one or more embodiments, finding the valleys of the profile as the candidates of the stent strut behind the lumen edge, and then searching and growing the local peaks to confirm that such local peaks are embedded stent struts); and (xi) outputting the smoothed lumen edge together with stent strut locations.

Figure 3:
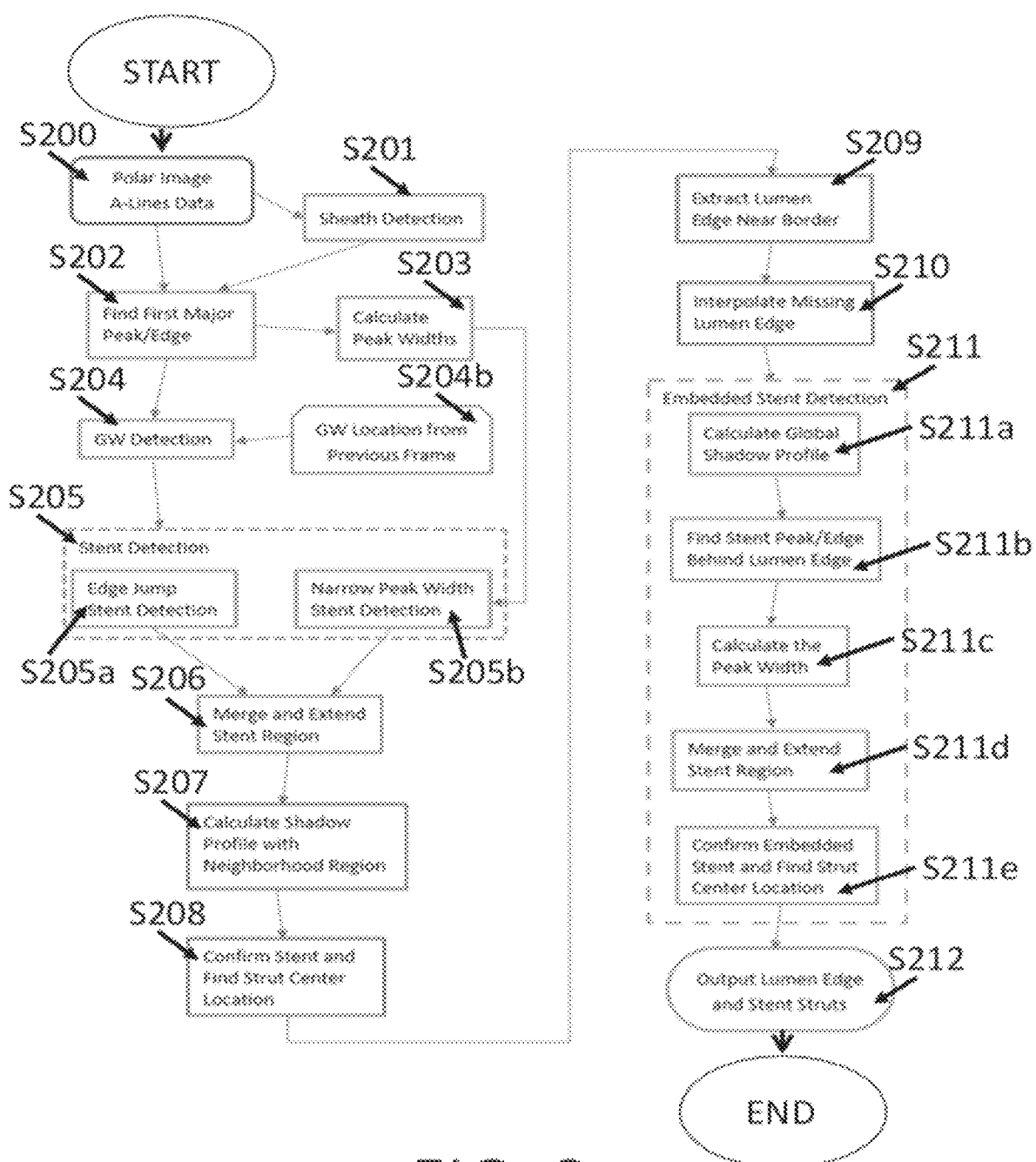
FIG. 3 is a flow diagram showing at least one embodiment of a lumen, stent, and/or artifact detection process in accordance with one or more aspects of the present disclosure.

In accordance with at least one aspect of the present disclosure and as aforementioned, one or more methods for lumen, stent, and/or artifacts detection of OCT images are provided herein. FIG. 3 illustrates a flow chart of at least one embodiment of a method for lumen(s), stent(s), and/or artifact(s) detection of OCT image(s). Preferably, the method(s) may include one or more of the following: (i) performing OCT image pre-processing to obtain/process Polar image A-lines data (e.g., using filtered OCT polar image data) (see e.g., step S200 in FIG. 3); (ii) performing sheath detection and/or excluding the sheath (see e.g., step S201 in FIG. 3); (iii) computing a peak and maximum gradient edge for each A-line and/or finding a major peak and/or edge (see e.g., step S202 in FIG. 3); (iv) finding and calculating peaks and width parameters for the lumen edge and artifacts (see e.g., step S203 in FIG. 3); (v) detecting/determining and removing a guide wire artifact (see e.g., step S204 in FIG. 3; see also, step S204b in FIG. 3 where a guidewire location determining may be based, at least in part, on a previous frame); (vi) identifying/detecting and/or processing the stent strut candidates using location and peak width jumps (e.g., using edge jump stent detection (see e.g., step S205a in FIG. 3), narrow peak width stent detection (see e.g., step S205b in FIG. 3), a combination thereof, etc.) (see e.g., step S205 in FIG. 3); (vii) merging and extending a stent region (see e.g., step S206 in FIG. 3); (viii) calculating a shadow profile of the stent strut candidates, finding a stent strut center (see e.g., step S208 in FIG. 3), and/or confirming a shadow pattern for the stent center location (see e.g., step S207 and/or step S208 in FIG. 3); (ix) extracting a lumen edge near the border or border region (see e.g., step S209 in FIG. 3); (x) interpolating missing lumen edge or missing lumen edge information/data (e.g., using linear interpolation) (see e.g., step S210 in FIG. 3); (xi) performing embedded stent detection (e.g., finding an embedded stent(s) and/or stent strut center(s)) (see e.g., step S211 in FIG. 3); and (xii) outputting and/or storing the lumen edge and/or stent strut center location(s) (see e.g., step S212 in FIG. 3). In one or more embodiments, the step of performing embedded stent detection (see e.g., step S211 in FIG. 3) may include one or more of the following: (a) calculating a global shadow profile (see e.g., step S211a in FIG. 3); (b) finding a stent peak/edge behind the lumen edge (see e.g., step S211b in FIG. 3); (c) calculating the peak width (see e.g., step S211c in FIG. 3); (d) merging and extending the stent region (see e.g., step S211d in FIG. 3); and/or (e) confirming the embedded stent and finding the strut center location (see e.g., step S211e in FIG. 3).

Figure 4B:
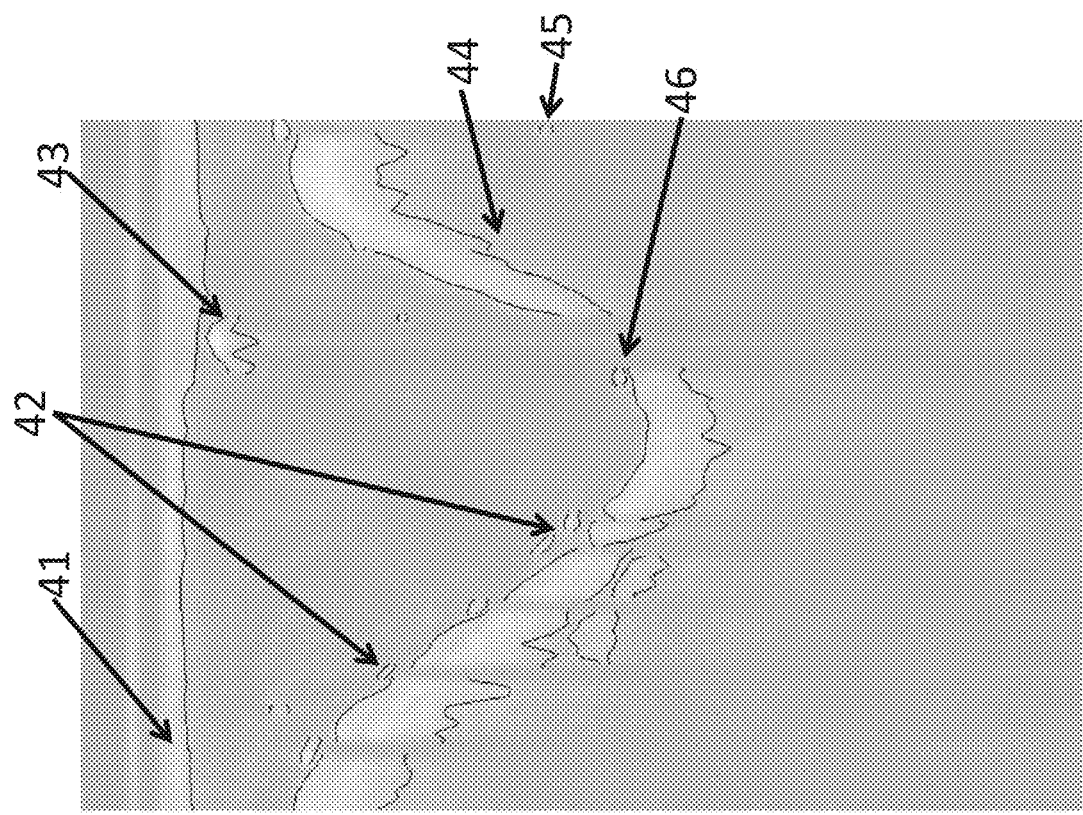
FIGS. 4A-4B are at least one embodiment example of an OCT image in Polar Coordinates taken of a target (e.g., a stented vessel) using at least one apparatus or system for performing lumen, stent, and/or artifacts detection techniques in accordance with one or more aspects of the present disclosure.
Figure 4A:
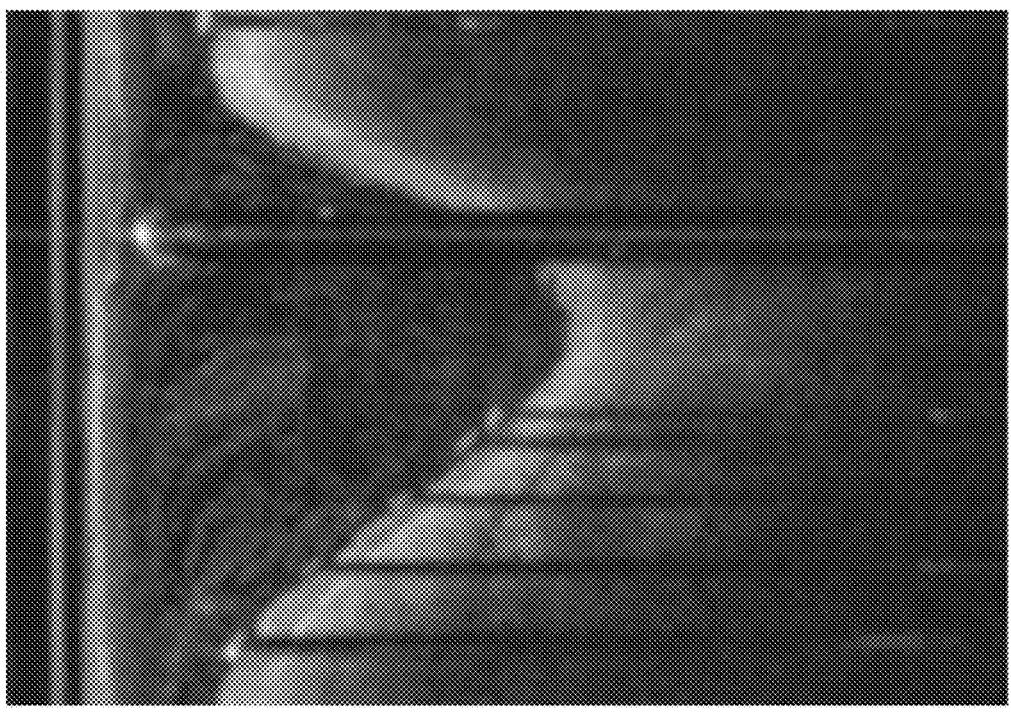

By way of at least one embodiment example of performing image pre-processing (e.g., OCT image pre-processing) to obtain/process Polar image A-lines data (e.g., using filtered OCT polar image data) (see e.g., step S200 in FIG. 3), reference is made to FIG. 4A. As shown in FIG. 4A, in at least one embodiment of an OCT image of a stented vessel in the Polar coordinate, a center of an imaging probe may be located at the top edge of the image. Each column of the image may constitute an A-line.

In accordance with at least one aspect of the present disclosure and as aforementioned, one or more additional methods for lumen, stent, and/or artifacts detection of OCT images are provided herein and are discussed in U.S. patent application Ser. No. 16/414,222, filed on May 16, 2019 and published on Dec. 12, 2019 as U.S. Pat. Pub. No. 2019/0374109, the entire disclosure of which is incorporated by reference herein in its entirety. By way of a few examples, pre-processing may include, but is not limited to, one or more of the following steps: (1) smoothening the 2D image in the Polar coordinate (e.g., using a Gaussian filter, as discussed below, etc.), (2) computing vertical and/or horizontal gradients using a Sobel operator (as otherwise discussed below, etc.), and/or (3) computing binary image using an Otsu method. For example, Otsu's method is an automatic image thresholding technique to separate pixels into two classes, foreground and background, and the method minimizes the intraclass variances between two classes and is equivalent to a globally optimal k-means (see e.g., https://en.wikipedia.org/wiki/Otsu%27s_method). One skilled in the art would appreciate that pre-processing methods other than Otsu's method (such as, but not limited to, Jenks optimization method) may be used in addition to or alternatively to Otsu's method in one or more embodiments.

By way of at least one embodiment example of sheath detection (see e.g., step S201 in FIG. 3), a Polar coordinate image (e.g., an OCT Polar coordinate image, such as, for example, the OCT image of FIG. 4A) may include (from the top side to the bottom side of FIG. 4A, from the top side to the bottom side of an OCT Polar coordinate image, etc.) a sheath area, and a normal field of view (FOV). In one or more embodiments, the lumen area and edge are within the FOV. Because one or more shapes of the sheath may not be a circle (as may be typically assumed) and because the sheath (and, therefore, the sheath shape) may be attached to or overlap with the lumen or guide wire, it may be useful to separate the sheath from the other shapes (e.g., the lumen, the guide wire, etc.) ahead of time.

By way of at least one embodiment example of computing/finding a peak and a major or maximum gradient edge (e.g., for each A-line) (see e.g., step S202 in FIG. 3), soft tissue and other artifacts may be presented on each A-line by one or more peaks with different characteristics, for example, in one or more embodiments of a lumen OCT image(s) (e.g., a normal lumen OCT image). For example, the soft tissue may have a wide bright region beyond the lumen edge, while the artifacts may produce an abrupt dark shadow area beyond the edge. Due to the high-resolution nature of one or more OCT images, transitions between neighbor A-lines may have signals for both peaks. Such signals may allow one or more method embodiments or processes to obtain more accurate locations of the artifact objects and/or the lumen edges.

Regardless of the approach, a predetermined or determined threshold may be used to detect the most significant pulse that may be corresponding to the lumen edge (in one or more embodiments, the most significant pulse denotes the maximum peak and its associated front edge also named as "major peak/edge"; such data may contain or include artifact edge pixels) in a specific A-line in one or more embodiments. Any pulse above the threshold is an edge pulse of an object candidate. The largest pulse among all the candidates in terms of area under the pulse is considered to be the maximum peak (also referred to herein as the "most significant pulse", or the "major peak/edge", etc.).

As depicted in FIG. 4B, the objects of lumen edge, stent, guide wire and other artifacts may be formed by connecting the neighbor peaks. The most significant pulses are connected and form segments of lumen edge objects which have a relatively thick range 44. Other peaks with relatively limited range while casting shadows are likely to be the stent struts shown as 42. Guide wire(s) formed by the significant pulses different in both location and shadow comparing to, or as compared with, the lumen edges are shown as 43. In addition to major peak/edge pair objects, other peaks may still exist and may form objects either before or after the lumen edges. Examples are (but are not limited to): metal reflection artifact object behind stent strut 45, a blood object which does not cast a strong shadow 46, etc. All the objects are aggregated based on peak and edge pulse results on each A-line, with the sheath object 41 predetected beforehand.

Figure 5:
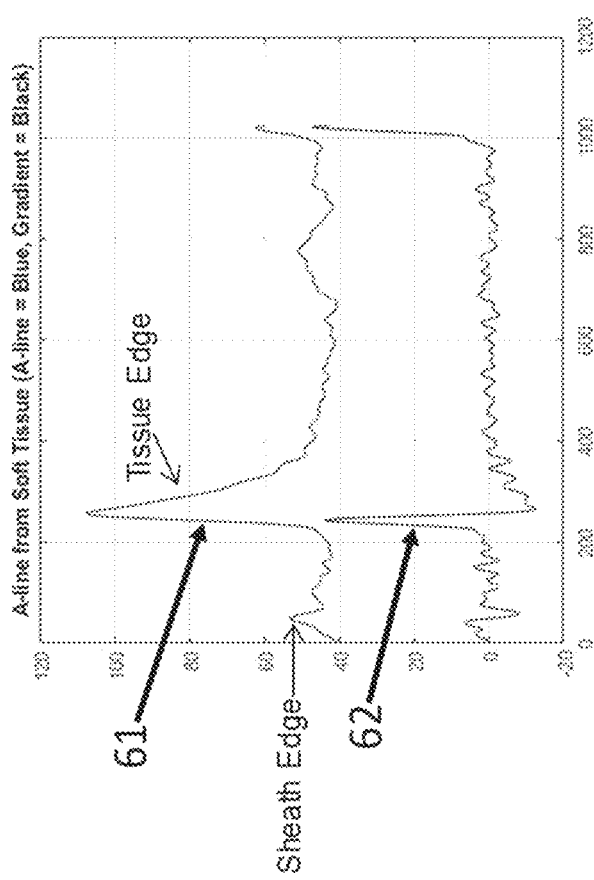
FIG. 5 is a graph showing smoothed A-line and gradient from a target (e.g., soft tissue) in accordance with one or more aspects of the present disclosure.

FIG. 5 shows at least one embodiment of an A-line intensity profile from soft tissue that may be plotted as a one-dimensional signal. The A-line signal 61 (i.e., the blue A-line, the top line of FIG. 5, etc.) has been smoothed by a 2D Gaussian filter for more reliable and accurate peak detection. The corresponding gradient 62 (i.e., the black gradient line, the bottom line of FIG. 5, etc.) along the A-line may also be filtered using a 1D filter for further smoothing in one or more embodiments. Preferably, in one or more embodiments, special care or step(s) may be taken to avoid any phase delay introduced by any filtering so that the pulse location is not shifted. After such filtering, a much smoother A-line signal may be obtained as depicted in FIG. 5. The smoothed, one-dimensional gradient along the A-line is also plotted in the same figure to show the correspondence between the pixel intensity and the one-dimensional gradient along the A-line. As shown in the embodiment example of FIG. 5, the lumen edge pixel is located at the rising edge of the intensity signal, which corresponds to the maximum peak location in the one-dimensional gradient signal. Signals from the catheter sheath may also be noticed in the smoothed A-line signal, and a sheath edge signal has much lower amplitude compared to that of the lumen edge signal in the embodiment of FIG. 5.

In one or more method embodiments, additional filtering (e.g., 1D filtering) may be performed to smooth A-lines and gradient(s) along A-lines (see step S302) of FIG. 8A discussed further below. In at least one embodiment, it should be noted that soft tissue has a wide bright region beyond the lumen edge while artifacts produce an abrupt dark shadow area beyond the edge. A typical A-line from the soft tissue may be plotted as a one-dimensional signal. The pulse in the one-dimensional signal may correspond to a vessel wall. The rising edge of the pulse may be where the edge pixel of the A-line lies. By detecting the edge pixel in each A-line, the two-dimensional edge detection issue is converted into a simpler one dimensional pulse detection issue. In other words, one or more embodiments of the present disclosure simplify the lumen edge, stent, and/or artifacts detection approach and provide a solution at the same time.

In one or more embodiments, an additional step of finding and calculating the peaks and width parameters for lumen edge, stent(s) and/or artifact(s) may be performed (see e.g., steps S202 and/or S203 in FIG. 3). In one or more embodiments, for each A-line signal, the highest peak is detected within the proper FOV range obtained in one or more embodiment examples of step S201 as discussed above. In at least one embodiment, there may be three (3) types of widths defined for the detected peak. The first may be a half-max width that may be detected using an adaptive threshold based on mean and maximum values of the smoothed A-line. By way of at least one embodiment example, the threshold may be computed, as follows:

Threshold=(mean+peak)/2, where "mean" is the average of the smoothed A-line and "peak" is the maximum value of the smoothed A-line. This threshold may be used to detect the most significant pulse corresponding to the lumen edge in a specific A-line. Any pulse above the threshold may be an edge pulse candidate in one or more embodiments. The largest pulse among all the candidates in terms of area under the pulse may be considered to be the maximum peak. The second width of the highest peak may be defined as the one dimensional gradient signal along the A-line in the vicinity of the maximum peak, and may be used to identify the exact location of the lumen edge point in the smoothed A-line. The third width of the same peak may be defined along the A-line similar to the second width. However, for the third width, the gradient value will drop from its peak value to zero, which indicates the point that the value change stops and begins reversing its direction. By placing together all the lumen edge points thus detected from all the A-lines in one or more embodiments, the lumen edge for the vessel is formed as a function of maximum peak locations vs. A-line indices.

In one or more embodiments, a guide wire artifact may be determined/detected and removed (see e.g., steps S204 and/or S204b in FIG. 3). In the presence of stent struts and guidewires, the lumen edge points of the soft tissue may be fully or partially obstructed. The lumen edge points detected from one or more of the aforementioned steps, such as, but not limited to steps S202 and/or S203, therefore may contain the edge points from the artifacts in the OCT image. These edge points may distort the lumen geometric parameter calculation, and, in one or more embodiments, may be removed to avoid such distortion and to obtain accurate parameters (preferably, in one or more embodiments, the subject edge points are removed before obtaining the accurate parameters).

Figure 6A:
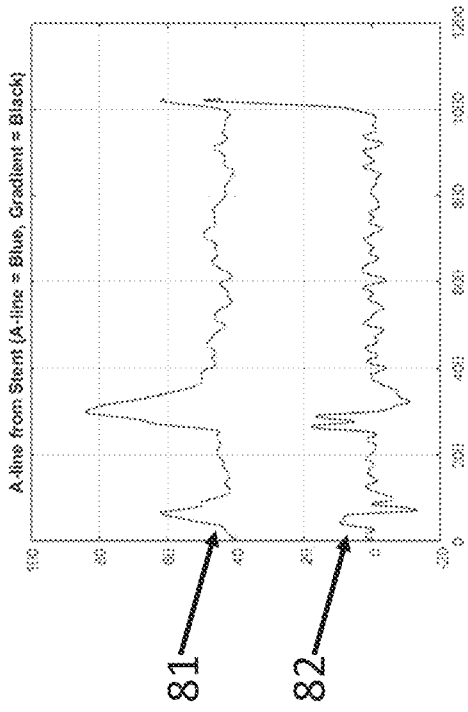
FIGS. 6A-6B depict graphs showing an A-line from a guidewire and an A-line from a stent strut, respectively, obtained using at least one apparatus or system for performing lumen, stent, and/or artifacts detection techniques in accordance with one or more aspects of the present disclosure.

FIG. 6A depicts an A-line 71 (i.e., the blue line, the top line of FIG. 6A, etc.) from a guidewire embodiment example. It is noticeable that the one-dimensional gradient signal 72 (i.e., the black line, the bottom line of FIG. 6A, etc.) has a steep minimum peak, which corresponds to the sharp falling intensity of the A-line signal 71 due to an opaqueness of the guidewire to the imaging laser beam and the relative large size of the guidewire. One should also notice that a width of the one-dimensional pulse is much narrower compared to the pulse signal from the soft tissue.

Figure 6B:
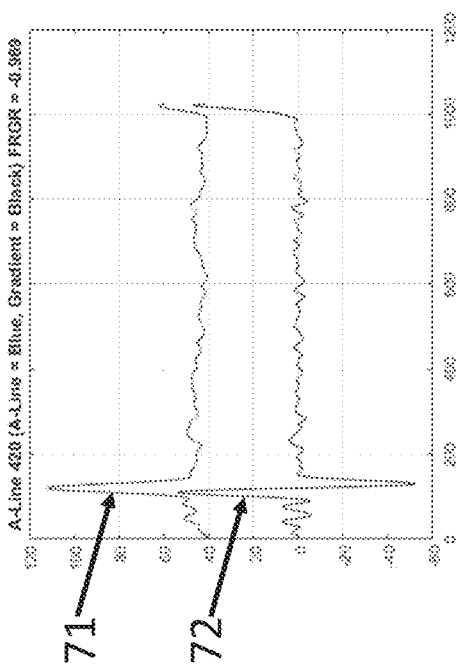

FIG. 6B depicts an A-line 81 (i.e., the blue line, the top line of FIG. 6B, etc.) from a stent strut embodiment example. It is noticeable that the pulse signal corresponding to the stent strut also produces a relatively larger falling peak compared to the rising peak in the one dimensional gradient signal 82 (i.e., the black line, the bottom line of FIG. 6B, etc.), though the peak is less pronounced compared to that from the guidewire signal 72 in FIG. 6A.

In both cases of FIGS. 6A and 6B, among the neighborhood A-line within the range of guide wire or stents, the first width and the second width of the peak are equal or are very close. The width values are also small and relatively unchanged comparing to the widths in the neighbor A-lines for lumen tissues. Therefore, the locations and the peak width jump between the neighbor A-lines may indicate a switch from an artifact object to the lumen edge. In the transition region between them, both objects may be present. The additional local peaks closer to the object other than the major peaks may be extracted by a peak search process similar to the aforementioned details/conditions of step(s) S204 and/or S204b, but on a more limited FOV region.

In one or more instances, a guide wire region may have a strong reflection, which corresponds to higher peak values. A guide wire region also may cover a larger range in terms of A-lines and often may have a strong reflection at the center A-lines. When a guide wire and stents both exist or are used in one or more embodiments, some stents struts may overlap with the guide wire, and the shadow regions may be extended by the stent(s). For those kind of conditions, identifying the guide wire correctly helps the further process to extract other stents.

One or more embodiments of the guide wire search process used for step(s) S204 and/or S204b may be defined as or may include one or more of the following: a) starting from the maximum peak values for all A-lines; b) growing the neighbor edge until either location or width jump finds a boundary point; c) continuing to grow around the boundary until the tissue only peak/edge pair is reached; d) growing back from the tissue only peak/edge pair until the end is reached; e) conducting the process on both directions; f) defining the range of the A-lines to include the tissue only peaks on both sides as the shadow range; g) calculating a shadow profile behind the tissue peaks to confirm the shadow does indeed exist; h) when the shadow is confirmed, the guide wire region is then confirmed; otherwise, iterate or repeat the process steps (a) to (h) with the next maximum peak value.

After the guide wire region has been identified, in one or more embodiments, the edge points may not be considered (and are, in one or more embodiments, preferably not considered) as the lumen edge and may be removed for stent detection step(s) that follow.

In one or more embodiments, stent detection may be performed (see e.g., step S205 in FIG. 3). For example, stents may be detected by identifying stent strut candidates using one or more techniques, such as, but not limited to, edge jump stent detection (see e.g., step S205a in FIG. 3), narrow peak width stent detection (see e.g., step S205b in FIG. 3), etc. By way of at least one further example, stent strut candidates may be identified using location and peak width jumps. Confirmation and removal of the stent strut obstructed lumen edge points may share similar steps as done for sheath and/or guide wire detection and removal, but in a more iterative approach in one or more embodiments. First, in at least one embodiment, the major peak and edge profile for the whole lumen may be obtained with the guide wire removed. When there is/are stent(s) present in front of the lumen edge, the edge position jumps may indicate the possible stent candidates. For stents which are very close to the lumen edge either on one side or both sides, the stents and/or stent candidates may be identified by looking into the profile of the peak widths. The stent strut peaks tend to have small and equal peak widths compared to neighbor lumen peaks and corresponding edges.

In one or more embodiments, stent detection may be performed by merging and extending a stent region (see e.g., step S206 in FIG. 3). Following the above lists or listing of stent strut candidates, in one or more embodiments, the search process may be conducted locally on each candidate to find the neighbor lumen edges on both sides of the stent strut. In at least one embodiment, the neighbor lumen edges are further extended until the connected peak and edge may no longer be confirmed to be a valid lumen edge. The covered region may be marked as confirmed edges. During one or more embodiments of the process, the candidates coming from different detection methods may have duplicates such that sets of candidates overlap. As such, the overlapping condition and the duplicates may be checked before proceeding on to the next step. Once all candidates are processed, the whole lumen edge circle may be marked as confirmed edges. Broken segments may be identified, and reasons for doing so are explained to at least confirm that the candidates and broken segments are all valid results.

In one or more embodiments, a shadow profile of the stent strut candidates may be calculated (see e.g., step S207 in FIG. 3) and/or a shadow pattern may be confirmed for an identified or found stent center location (see e.g., step S208 in FIG. 3). For each stent, the interpolated lumen edge exists between lumen edges on each of the sides, which is behind the detected peak and edge of the stent, in one or more embodiments. Based on the interpolated lumen peak position, the shadow accumulation profile may be calculated. In at least one embodiment, a normal shape of the shadow accumulation profile or shadow profile may be a single valley with a nadir (e.g., foot, base, lowest point, etc.) at, substantially at, or near the center of the valley. The minimum value location may be identified as the stent center, which corresponds to a middle of the stent strut that casted the shadow. There may exist some second reflection behind the stent shadow, which may distort the true shadow profile, in one or more embodiments. An additional process may be employed to remove the effects of such second reflections behind the stent shadow by identifying the narrow width peaks behind the interpolated lumen edge within the shadow and subtracting them from the original image.

In one or more embodiments, a lumen edge near the border may be extracted (see e.g., step S209 in FIG. 3). As extra steps when processing each stent strut candidates, there may be one or more valid lumen edges that exist as secondary peaks behind the stent peak near the border region. Proper extraction and inclusion of the one or more valid lumen edges that exist as secondary peaks behind the stent peak improves the quality of the lumen edge results. This is one of the several unique aspects or features or improvements of the present disclosure compared to other methods because all such A-line results are often thrown away. The extraction of such a lumen edge may be based on the connectivity of the current lumen edge by searching a secondary peak outside of the major peak on the neighborhood A-line that already has been identified or that is identified as the non-lumen peak. The process may search on both sides of the stent neighborhood A-lines until no further peak is found in one or more embodiments.

In one or more embodiments, any missing portion of the lumen edge may be interpolated to fill in missing data (see e.g., step S210 in FIG. 3). For each confirmed stent location, any gap between or in the lumen edge may be filled using linear interpolation. Both lumen peak and edge information are kept and interpolated in one or more embodiments. After the process, the whole lumen circle may be processed and may form a closed circle-like curve for the lumen edge.

In one or more embodiments of embedded stent detection (see e.g., step S211 in FIG. 3), the peak curve may be similar and may be used to calculate a shadow accumulation profile or a shadow profile for the whole image (see e.g., step S211a in FIG. 3). In one or more embodiments, finding an embedded stent and/or stent strut center may be based on the lumen peak curve generated above in step S209 and/or S210. The shadow accumulation profile or shadow profile may be generated based on lumen peak location and a maximum thickness available inside the FOV for each A-line in one or more embodiments. In such a shadow accumulation profile or shadow profile, in one or more embodiments, a significant valley may indicate a shadow region that may be an embedded stent strut. In one or more embodiments of embedded stent detection (see e.g., step S211 in FIG. 3), a stent peak and/or edge behind the lumen edge may be found (see e.g., step S211b in FIG. 3). In one or more embodiments of embedded stent detection (see e.g., step S211 in FIG. 3), a peak width and/or thickness may be calculated (see e.g., step S211c in FIG. 3). In one or more embodiments of embedded stent detection (see e.g., step S211 in FIG. 3), the stent region may be merged and extended (see e.g., step S211d in FIG. 3). In one or more embodiments of embedded stent detection (see e.g., step S211 in FIG. 3), an embedded stent(s) may be confirmed and extracted, and struts location information may be determined/identified. Following the above discussed steps, for example, to identify and confirm the stent struts, valid embedded stents may be extracted and confirmed, with its location information (such as, but not limited to, strut center location) identified as well.

In one or more embodiments, the lumen edge may be output and/or the stent strut center location (and/or other stent strut location information) may be output (see e.g., step S212 in FIG. 3). After applying a 1D smoothing filter on the lumen edge results, the lumen edge and/or stent strut center location information (and/or other stent strut location information) may be output to a desired format, may be stored in a memory, may be printed, may be displayed on a display, etc.

One or more embodiments may detect the peaks and edges with three types of peak widths in each one-dimensional data (A-line). In one or more embodiments, the maximum peak in each of the A-lines may be detected. The most significant pulse denotes the maximum peak and its associated front edge also named as "major peak/edge" in each of the A-lines in one or more embodiments. In one or more embodiments, a gradient of one-dimensional data (A-line) may be used to determine the edge location associated with each peak. In one or more embodiments, each peak may associate with three types of width: (1) a half-max width, (2) max gradient width, and (3) minimal value width, which defines the peak range on the A-line. The half-max width, which is the first width, may be used to test connectivity between neighbor peaks. The max gradient width, which is the second width, may be used to indicate a thickness of the object. The minimal value width, which is the third width, may be used to define the peak range. In one or more embodiments, other peaks may exist outside of a current peak range. One or more embodiments may group connected peaks on different neighbor A-lines together to form geometrically separate objects in 2D space.

One or more embodiments may distinguish the lumen edge peak from the guide wire and stent struts. For example, in one or more embodiments, disconnected major peaks in neighbor A-lines may indicate separate objects, such as a lumen edge peak and a guide wire or stent strut(s). The peak location connectivity may exist in a case where the stent strut peak edge is very close to the lumen edge in neighbor A-lines. In such cases, the lumen and stent may be separated by the jump of the peak widths. In one or more embodiments, peak widths of stent strut(s) are small and near constant, including the first, second, and third widths, because of a shadow behind the stent strut(s). Therefore, both peak location and the peak widths' values are used to separate the objects, such as a lumen edge peak and a guide wire or stent strut(s).

One or more embodiments of the present disclosure may grow major peaks into neighbor A-lines around the boundary region between the lumen and the stent strut(s) or guide wire. Multiple peaks may exist when peaks from a neighbor A-line grow by searching a local peak which is outside the major peak on the current A-line. Both a lumen edge region and stent strut objects may be grown into more complete objects that leads to an improved, optimal, and/or correct decision of the boundary between the lumen and the stent strut(s) or guide wire (which may be useful in one or more situations, including, but not limited to, some challenging cases).

One or more embodiments of the present disclosure may calculate the shadow accumulation profile (or shadow profile) locally based on the interpolation of lumen peaks on both sides of the guide wire and/or stent strut(s). In one or more embodiments, the interpolation may happen on both sides of the guidewire and the stent struts. Interpolation of lumen edge peaks may be used to calculate the shadow profile because starting points for the accumulation calculation may be critical and/or may substantially improve the accuracy in one or more embodiments. A shape of the shadow profile may be used to confirm or ensure that the area includes or contains a valid shadow. As aforementioned, a single valley shadow may be used to find a center location for a stent strut(s).

One or more embodiments may process stent candidates iteratively to complete the lumen profile for the whole image. A guide wire region may be processed first, and then each stent candidate may be processed locally for better accuracy. Both lumen peak and lumen edge curves may be generated to confirm the results.

One or more embodiments of the present disclosure may use a global lumen peak curve to calculate the shadow profile and to detect embedded stent(s). An interpolated peak curve may be used to calculate the global shadow profile in one or more embodiments, and/or the global shadow profile may be used to identify the embedded stent strut(s). In one or more embodiments, embedded stent strut(s) may be extracted using a secondary peak width pattern.

Additionally or alternatively, in one or more embodiments, a principal component analysis method and/or a regional covariance descriptor(s) may be used to detect objects, such as stents. Cross-correlation among neighboring images may be used to improve lumen edge detection result(s). One or more embodiments may employ segmentation based image processing and/or gradient based edge detection to improve detection result(s).

Figure 7B:
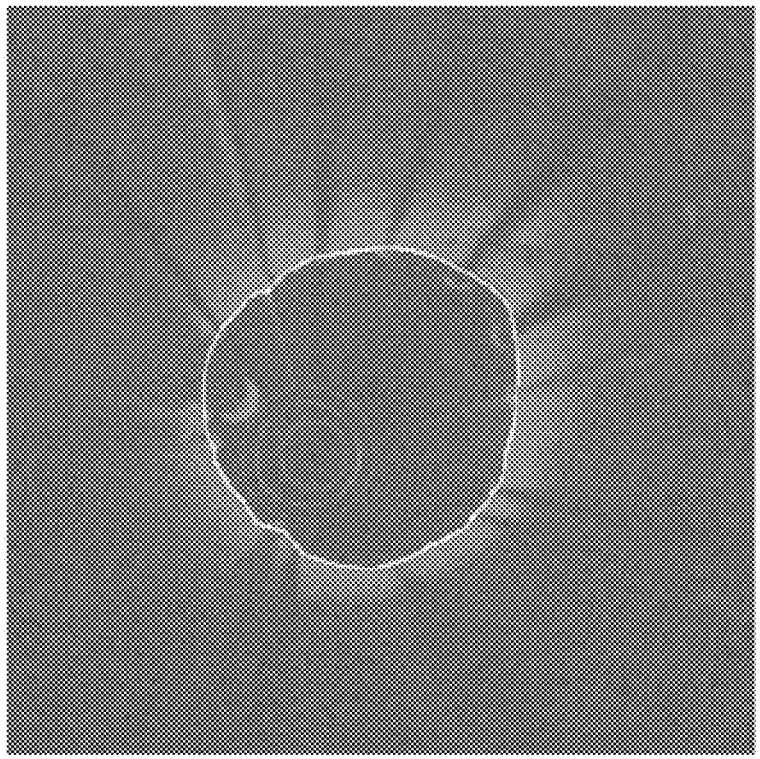
FIGS. 7A-7B show a pair of an OCT image in polar coordinates taken of a target (e.g., a stented vessel) and an OCT image in Cartesian coordinates, respectively, using at least one apparatus or system for performing lumen, stent, and/or artifacts detection techniques in accordance with one or more aspects of the present disclosure.
Figure 7A:
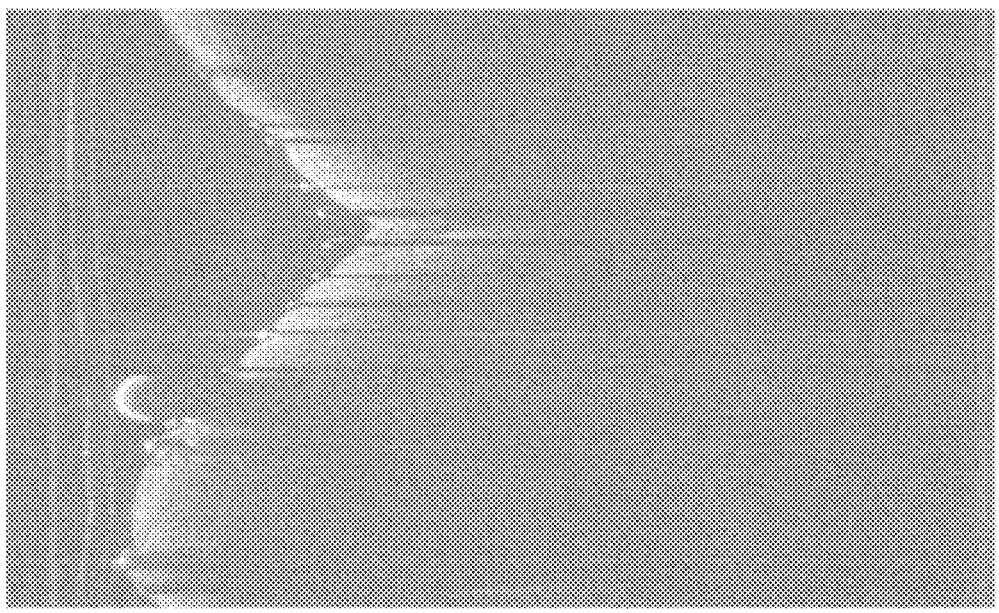

As shown in FIG. 7A, the OCT image in polar coordinates (e.g., of a stented vessel) may be displayed vertically (the same as shown, for example, in FIG. 4A), and/or may be displayed with a corresponding OCT image in Cartesian Coordinates (see e.g., FIG. 7B) using at least one apparatus or system for performing lumen, stent, and/or artifacts detection techniques in accordance with one or more aspects of the present disclosure.

In accordance with at least one aspect of the present disclosure and as aforementioned, one or more additional methods for lumen, stent, and/or artifacts detection of OCT images are provided herein, or may be used with one or more of the features or aspects of the present disclosure, and are discussed in U.S. patent application Ser. No. 16/414,222, filed on May 16, 2019 and published on Dec. 12, 2019 as U.S. Pat. Pub. No. 2019/0374109, the entire disclosure of which is incorporated by reference herein in its entirety. For example, FIG. 8A illustrates a flow chart of at least one embodiment of a method for lumen, stent, and/or artifacts detection of OCT image(s). Preferably, the method(s) may include one or more of the following: (i) performing two dimensional (2D) image smoothing (e.g., using a lowpass filter, using a Gaussian filter, etc.) (see step S300 of FIG. 8A); (ii) computing image vertical and horizontal gradients (see step S301 of FIG. 8A); (iii) smoothing A-lines and gradient along A-lines (e.g., using one dimensional (1D) filtering) (see step S302 of FIG. 8A); (iv) detecting a lumen edge point(s) in each A-line from the most significant pulse (e.g., the most significant pulse may be the pulse with the highest amplitude or the pulse with the largest underlying area determined by applying a size criterion or size criteria (e.g., width criterion, area under the pulse criterion, etc.) where different size criteria may produce similar results) (see step S303 of FIG. 8A); (v) removing edge points corresponding to a large falling and rising gradient ratio (FRGR) (e.g., the most significant pulse in the A-line that has a steep falling edge comparable to the rising edge, that produces a larger FRGR value, etc.) and small sized pulses (e.g., the most significant pulse in the A-line with the pulse amplitude or the area underlying the pulse below a threshold, etc.) (see step S304 of FIG. 8A); (vi) removing edge point(s) corresponding to multi-peak pulse(s) (see step S305 of FIG. 8A); (vii) removing edge point(s) corresponding to multi-pulse A-line(s) (see step S306 of FIG. 8A); (viii) filling the gaps in the lumen edge using interpolation (e.g., via median filtering the lumen edge) to form the lumen edge (e.g., forming the lumen edge from the most significant pulse locations of all the A-lines) (see step S307 of FIG. 8A); (ix) filtering or smoothing the lumen edge (e.g., using low pass filtering, such as 1D lowpass filtering and/or median filtering, etc.) (see step S308 of FIG. 8A); and (x) converting the lumen edge into Cartesian coordinates (see step S309 of FIG. 8A).

In one or more OCT images of a stented vessel in the polar coordinates (best shown in different lumen detection, stent detection, and/or artifact detection embodiment examples, including, the image of FIG. 7A), the center of the imaging probe may be located at the top edge of the image. Each column of the image constitutes an A-line in one or more embodiments. That said, as aforementioned, the center of the imaging probe may be located at a side edge of an image where each row of the image constitutes an A-line in one or more embodiments (see e.g., FIG. 4A as discussed above). Preferably, in at least one embodiment, the OCT image in polar coordinates is filtered using a two dimensional low pass Gaussian filter (see e.g., step S300 in FIG. 8A) to smooth out the inter A-line noise as well as some of the intra A-line noise in order to reduce and/or remove the overall noise in the image.

Figure 8A:
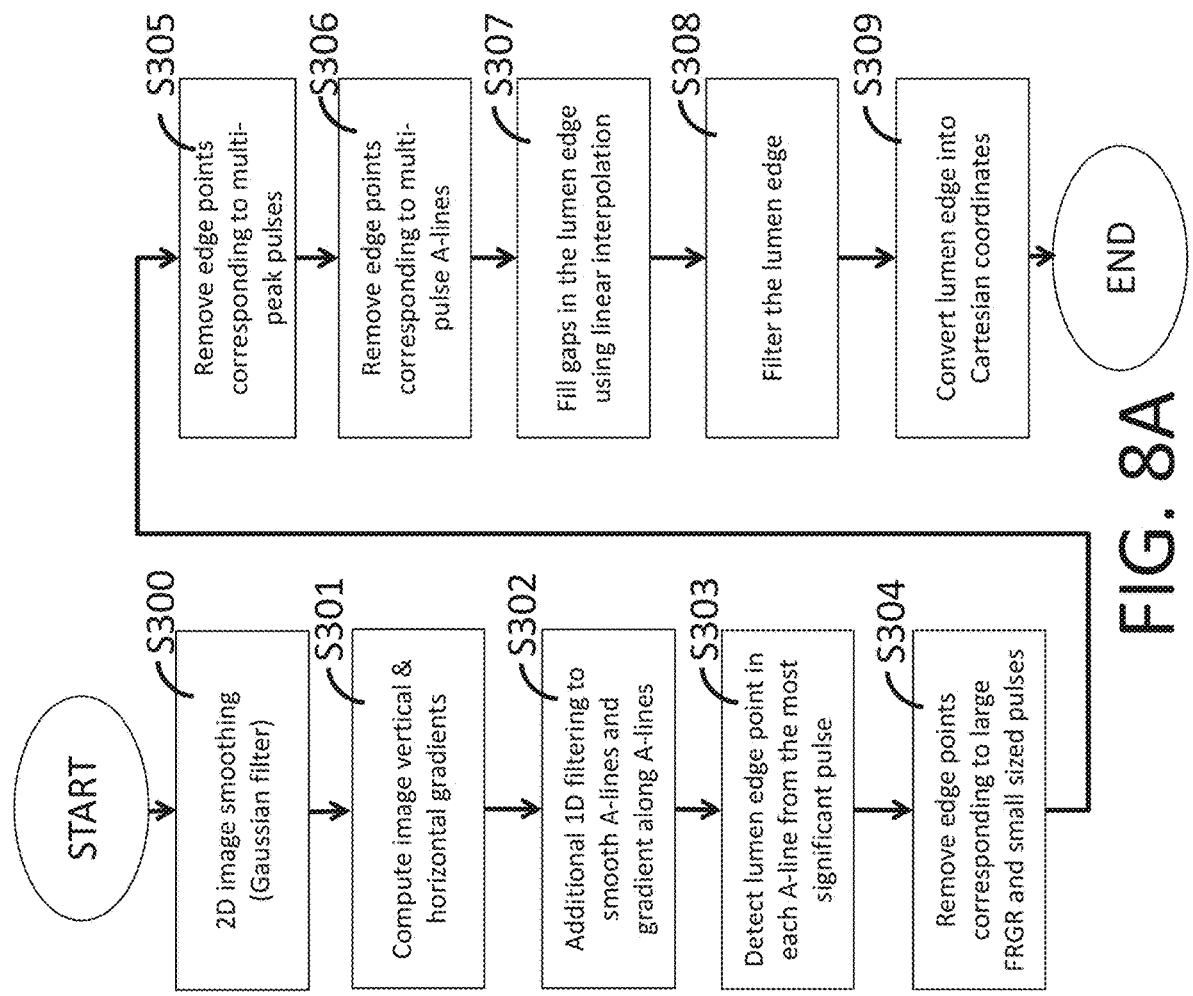
FIGS. 8A-8B are flow diagrams showing respective embodiments of at least two lumen, stent, and/or artifacts detection processes in accordance with one or more aspects of the present disclosure.

In one or more method embodiments, image vertical and horizontal gradients are preferably computed (see step S301 of FIG. 8A). In one or more embodiments, a convolution operation operator Kernel (K), may be used such that G=K⊗A, where ⊗ denotes a convolution operation. In at least one embodiment, the vertical gradient of the image may be calculated, for example, by applying the vertical Sobel operator (e.g., as one embodiment example of the Kernel K) to the smoothed image obtained from step S300:

$$G_y = \begin{bmatrix} 1 & 4 & 6 & 4 & 1 \\ 2 & 8 & 12 & 8 & 2 \\ 0 & 0 & 0 & 0 & 0 \\ -2 & -8 & -12 & -8 & -2 \\ -1 & -4 & -6 & -4 & -1 \end{bmatrix} \otimes A,$$

where A is the smoothed image from [Step 1], $G_x$ and $G_y$ are the horizontal and vertical gradients, and ⊗ denotes the 2D convolution operation. In at least one embodiment, the horizontal gradient of the image may be calculated, for example, by applying the horizontal Sobel operator (e.g., as one embodiment example of the Kernel K) to the smoothed image obtained from step S300:

$$G_x = \begin{bmatrix} -1 & -2 & 0 & 2 & 1 \\ -4 & -8 & 0 & 8 & 4 \\ -6 & -12 & 0 & 12 & 6 \\ -4 & -8 & 0 & 8 & 4 \\ -1 & -2 & 0 & 2 & 1 \end{bmatrix} \otimes A,$$

where A is the smoothed image from [Step 1], $G_x$ and $G_y$ are the horizontal and vertical gradients, and ⊗ denotes the 2D convolution operation. Each column in $G_y$ provides the gradient along an A-line while each row in $G_x$ provides the gradient across A-lines. The image vertical and horizontal gradients may also be computed using lower order Sobel operators as:

$$G_x = \begin{bmatrix} -1 & 0 & 1 \\ -2 & 0 & 2 \\ -1 & 0 & 1 \end{bmatrix} \otimes A, \text{ and}$$

$$G_y = \begin{bmatrix} 1 & 2 & 1 \\ 0 & 0 & 0 \\ -1 & -2 & -1 \end{bmatrix} \otimes A,$$

wherein A is the smoothed at least one image, $G_x$ and $G_y$ are the horizontal and vertical gradients, ⊗ denotes a two dimensional (2D) convolution operation, and each column in $G_y$ provides the gradient along an A-line while each row in $G_x$ provides the gradient across A-lines. Other possible operators that may be used here are the Prewitt operators as:

$$G_x = \begin{bmatrix} -1 & 0 & 1 \\ -1 & 0 & 1 \\ -1 & 0 & 1 \end{bmatrix} \otimes A, \text{ and}$$

$$G_y = \begin{bmatrix} 1 & 1 & 1 \\ 0 & 0 & 0 \\ -1 & -1 & -1 \end{bmatrix} \otimes A,$$

wherein A is the smoothed at least one image, $G_x$ and $G_y$ are the horizontal and vertical gradients, ⊗ denotes a two dimensional (2D) convolution operation, and each column in $G_y$ provides the gradient along an A-line while each row in $G_x$ provides the gradient across A-lines.

In one or more method embodiments, additional filtering (e.g., 1D filtering) may be performed to smooth A-lines and gradient(s) along A-lines (see step S302) of FIG. 8A. In at least one embodiment, it should be noted that soft tissue has a wide bright region beyond the lumen edge while artifacts produce an abrupt dark shadow area beyond the edge. A typical A-line from the soft tissue may be plotted as a one-dimensional signal. The pulse in the one-dimensional signal corresponds to the vessel wall. The rising edge of the pulse is where the edge pixel of the A-line lies. By detecting the edge pixel in each A-line, the two-dimensional edge detection issue is converted into a simpler one-dimensional pulse detection issue. In other words, one or more embodiments of the present disclosure simplify the lumen edge and artifacts detection approach and provide a solution at the same time.

Taking advantage of the flexibility in 1D signal processing, low pass and high pass 1D filtering may be applied to the A-line signal, in one or more embodiments, to remove the signal offset as well as to further smooth the A-line signal for more reliable pulse detection. The corresponding gradient along the A-line also may be filtered using a 1D filter for further smoothing. Preferably, any phase delay introduced by any filtering is avoided so that the pulse location is not shifted. For example, each A-line may be independently processed by applying 1D high pass filtering to remove a background and by applying low pass filtering to reduce noise.

After such filtering, a much smoother A-line signal may be obtained (see e.g., line 61 of FIG. 5). The smoothed one-dimensional gradient along the A-line is also plotted (see line 62 of FIG. 5) to show the correspondence between pixel intensity and the one-dimensional gradient along the A-line. In one or more embodiments (see e.g., FIGS. 5-6B), the Y-axis may be shown with arbitrary units (A.U.), and a pixel index (e.g., about 7 micron per pixel, about 5 micron per pixel, etc.) may be used for the X-axis. As shown in FIG. 5, the lumen edge pixel is located at the rising edge of the intensity signal, which corresponds to the maximum peak location in the one-dimensional gradient signal. Signals from the catheter sheath also may be noticed in the smoothed A-line signal (see Sheath Edge designation in FIG. 5), and the catheter sheath signal has much lower amplitude compared to that of the lumen edge signal.

In one or more method embodiments, detection of the lumen edge point in each A-line from the most significant pulse may be performed to create lumen edge data (see step S303) of FIG. 8A. In one or more embodiments, the lumen edge data may contain or include artifact edge pixels. There are numerous ways to perform this step. For example, for each A-line signal, the most significant pulse therein may be detected using an adaptive threshold. Based on the mean and the maximum values of the smoothed A-line, a simple threshold may be computed as:

Threshold=(mean+peak)/2, where "mean" is the average of the smoothed A-line and "peak" is the maximum value of the smoothed A-line.

As a further example, another approach to find the threshold is to find the average between the max peak and min peak as:

Threshold=(min+peak)/2.

A further alternative approach is to find the threshold based on the max peak as:

Threshold=(peak)×2/3.

Regardless of the approach, the predetermined or determined threshold is used to detect the most significant pulse corresponding to the lumen edge (in one or more embodiments, the lumen edge data may contain or include artifact edge pixels) in the specific A-line. Any pulse above the threshold is an edge pulse candidate. The largest pulse among all the candidates in terms of area under the pulse is considered to be the maximum peak (or the "most significant pulse"). The location of the highest peak of the one dimensional gradient signal along the A-line in the vicinity of the maximum peak is used to identify the exact location of the lumen edge point in the smoothed A-line. Again, in one or more embodiments, the lumen edge data may contain or include artifact edge pixels.

Placing together all the lumen edge points thus detected from all the A-lines forms the lumen edge (in one or more embodiments, the lumen edge data may contain or include artifact edge pixels) for the vessel as a function of maximum peak locations vs. A-line indices.

In one or more method embodiments, edge points corresponding to large FRGR and small sized pulses may be removed (see step S304) of FIG. 8A. In other words, artifact edge pixel(s) contained or included in the lumen edge pixel(s) may be removed using FRGR.

For example, in the presence of stent struts and guidewires, the lumen edge points of the soft tissue may be fully or partially obstructed. The lumen edge points detected from Step S303 may contain the edge points from the artifacts in the OCT image. In one or more embodiments, these edge points will distort the lumen geometric parameter calculation and preferably are removed before accurate or more accurate parameters may be obtained.

FIG. 6A depicts an example A-line from a guidewire (see smooth line 71; gradient of the A-line from the guidewire is shown by the line 72). As seen in FIG. 6A, it is noticeable that the one-dimensional gradient signal (see line 72) has a steep minimum peak, which corresponds to the sharp falling intensity of the A-line signal (see line 71) due to the opaqueness of the guidewire to the imaging laser beam and the relative large size of the guidewire. The width of the one dimensional pulse is much narrower as shown in FIG. 6A compared to the pulse signal from the soft tissue as shown in FIG. 5.

FIG. 6B depicts an example A-line from a stent strut (see smooth line 81; gradient of the A-line from the stent is shown by the line 82). As seen in FIG. 6B, it should be noted that the pulse signal corresponding to the stent strut also produces a relatively larger falling peak compared to the rising peak in the one dimensional gradient signal, though it is less pronounced compared to that from the guidewire as shown in FIG. 6A.

Based on these signatures (as shown in FIGS. 6A-6B), the falling and rising gradient ratio (FRGR) may be introduced as a measure of opaqueness and reflectivity of the imaged object or target. An A-line signal from a guidewire has a large falling and rising ratio, and so does an A-line from a stent strut. On the other hand, an A-line from the soft tissue has a smaller falling and rising gradient ratio.

The falling and rising gradient ratio may be used as an indicator of the stent strut and guidewire presence if the detected lumen edge and its corresponding falling rising gradient ratio are plotted together as discussed in U.S. patent application Ser. No. 16/414,222, filed on May 16, 2019 and published on Dec. 12, 2019 as U.S. Pat. Pub. No. 2019/0374109, the entire disclosure of which is incorporated by reference herein in its entirety.

Besides the noticeable differences of falling and rising gradient ratio values in the A-line signals from artifacts and soft tissue, it should be noted that the pulse size from the soft tissue and the pulse size from the artifacts display a noticeable difference. In one or more embodiments, one may use either the pulse width or the area under the 1D signal pulse as the measure of the signal pulse size as discussed in U.S. patent application Ser. No. 16/414,222, filed on May 16, 2019 and published on Dec. 12, 2019 as U.S. Pat. Pub. No. 2019/0374109, the entire disclosure of which is incorporated by reference herein in its entirety.

Using the noticeable differences of the falling raising gradient ratio and the differences in a size of the A-line pulses, the artifact region locations corresponding to the guidewire and stent struts in the detected lumen edge may be identified using simple thresholding where the threshold may be set, for example, as:

Pulse Size Threshold=mean−sigma*$k1$

Or

FRGR Threshold=mean+sigma*$k2$, where "mean" and "sigma" are the mean and standard deviation of the corresponding signal, and k1, k2 are empirical parameters preferably chosen, but not limited to, between 1 to 2.

An alternative approach to calculate the thresholds may be:

Pulse Size Threshold=mean+(peak−mean)/3

Or

FRGR Threshold=mean+(peak−mean)/3

Furthermore, as another alternative, the thresholds may also be calculated as:

Pulse Size Threshold=peak−(peak−mean)/2

Or

FRGR Threshold=peak−(peak−mean)/2

Preferably, in one or more embodiments, these identified edge points are not considered as the lumen edge and are not used for lumen parameter calculation.

In one or more method embodiments, edge points corresponding to multi-peak pulses may be removed (see step S305) of FIG. 8A. At least two examples for performing this step are discussed herein. For example, lumen edge data that corresponds to the boundary region between the soft tissue and the stent struts or other artifacts may be removed using multi-peak pulses. However, such multi-peak pulses may present or be present in a non-boundary region as well. Then the average horizontal gradient(s) are/may be used to identify the non-boundary region in such cases.

There may be diffraction and scattering around the edges of stent struts and of the guidewire. The diffraction and scattering effect produces some boundary regions between the soft tissue and the artifacts where the detected lumen edge may be distorted. Furthermore, since the A-lines used for producing the lumen edge are preferably filtered using a 2D filter in step S300, the boundary regions may be further smeared and extended. To completely remove the artifact effects on the lumen edge, these boundary regions are preferably removed from the detected lumen edge.

One advantage of using one dimensional A-line signal processing for lumen edge detection is that there may be a multi-peak pattern of these boundary regions from the A-line signal because both stents and lumen edge peaks exist in the A-line signal. For example, as discussed in U.S. patent application Ser. No. 16/414,222, filed on May 16, 2019 and published on Dec. 12, 2019 as U.S. Pat. Pub. No. 2019/0374109, the entire disclosure of which is incorporated by reference herein in its entirety, the boundary region may produce clustered multi-peak pulses in the A-line signal. Multi-peak pulses may be detected using the same threshold used in the maximum peak detection step S303 as discussed above, and is not repeated herein as a result. If a falling edge of a peak rises again before the falling edge falls below the threshold, a multi-peak pulse is considered to be identified in at least one embodiment. Preferably, if a pulse is detected as a multi-peak pulse, the lumen edge data from that A-line may be considered as the boundary region of the stent struts and guidewire and removed from lumen edge detection. In one or more embodiments, multi-peaks not in the boundary region may be retained, and are preferably retained in one or more embodiments.

Even if a falling edge of a peak falls below the threshold and then raises again to form another peak, it may still be considered as a multi-peak pulse. The correct identification of the lumen edge may then rely on the major peak detection and the size of the front peak in at least one embodiment. If the front peak is identified as the artifacts, such as, but not limited to, a stent or guidewire, the second peak may be the lumen edge. There may be small vessel branch presented in the tissue underneath the vessel wall, which may end up manifesting as two separate peaks in a single A-line in a similar manner in one or more embodiments. In such a case, the front peak without the narrow width may be the lumen edge. At least one way to distinguish multi-peak pulses between the valid lumen edge versus an influence of one or more artifacts is determining whether they are located within the boundary regions. Therefore, the multi-peak cases may be further classified into the non-boundary region and boundary region cases, and they may be removed from the detected lumen edge only in the boundary regions.

By way of another example and alternative to the aforementioned example, horizontal gradients may be used to identify and remove the lumen edge data corresponding to the boundary region between the soft tissue and narrow artifacts. In at least one embodiment, another method to identify the boundary region utilizes the gradient variation along the horizontal direction, for example, in FIG. 7A (figures in Polar Coordinate) (across the A-lines) in the region behind the detected lumen edge (additionally or alternatively, a gradient variation along a vertical direction, for example, in FIG. 4A may be used). As discussed in U.S. patent application Ser. No. 16/414,222, filed on May 16, 2019 and published on Dec. 12, 2019 as U.S. Pat. Pub. No. 2019/0374109, the entire disclosure of which is incorporated by reference herein in its entirety, a gradient across the A-lines may display a pattern of many shadows (which may include one or more artifact shadows) caused by the light blocking artifacts.

For each detected lumen edge point, the average values of across the A-lines gradient below the edge point may be computed as discussed in U.S. patent application Ser. No. 16/414,222, filed on May 16, 2019 and published on Dec. 12, 2019 as U.S. Pat. Pub. No. 2019/0374109, the entire disclosure of which is incorporated by reference herein in its entirety. These average values reflect the locations of the shadows caused by the light blocking artifacts. Given the directional property of the gradient across the A-lines, the bright to dark edge produces a rising peak while the dark to bright edge produces a falling peak. For each dark shadow produced by the stent strut, the shadow is bordered by a rising peak at one side and by a falling edge at the other side.

The boundary regions may therefore be identified as the area surrounded by the rising and falling peaks in the averaged values of across A-lines gradient next to the immediate artifact regions identified in step S304. In step S304, thresholds may be used to identify the center locations of artifacts, and the boundary regions delineated by the falling and rising peaks in step S305 may help remove the artifact region more completely or completely. The boundary regions identified by the falling and rising peaks of the average horizontal gradient may be used to distinguish the multi-peak pulse that may or may not be associated with a boundary region, and, in one or more embodiments, only those multi-peak pulses falling inside the boundary region may be removed from the lumen edge detection.

In one or more method embodiments, edge points corresponding to multi-pulse A-lines may be removed (see step S306) of FIG. 8A. For example, lumen edge data corresponding to a ghost signal or ghost signals produced (e.g., from reflection(s) of stent(s), any signal(s) other than the targeted signal, a luminance signal, etc.) may be identified and removed by detecting multiple pulses.

When there is strong reflection caused by the stent struts or guidewire, there may be a ghost signal or signals in the A-line signal due to a detected multipath signal. As another advantage of using one dimensional A-line signal processing for lumen edge detection, this ghost signal (or signals) manifests itself as an additional pulse signal in the A-line signal as discussed in U.S. patent application Ser. No. 16/414,222, filed on May 16, 2019 and published on Dec. 12, 2019 as U.S. Pat. Pub. No. 2019/0374109, the entire disclosure of which is incorporated by reference herein in its entirety. For example, an A-line plot may show two peaks in which the right peak corresponds to the ghost signal and the left peak corresponds to a stent strut as discussed in U.S. patent application Ser. No. 16/414,222, filed on May 16, 2019 and published on Dec. 12, 2019 as U.S. Pat. Pub. No. 2019/0374109, the entire disclosure of which is incorporated by reference herein in its entirety. Peaks of all significant pulses in the A-line signal may be determined.

Given that the most likely sources of strong reflection are stent struts and guidewire, the detected lumen edge points corresponding to the A-lines with a ghost signal (or signals) are preferably excluded from the parameter calculation for the lumen.

In one or more method embodiments, a lumen edge may be formed (see step S307) of FIG. 8A. For example, after removing all the artifacts from the detected lumen edge (e.g., edge points with a narrow pulse width (which correspond to edge points from guide wire(s) and stent(s)) may be removed; edge points with large FRGR (which correspond to edge points from weak stent(s)) may be removed; edge points with separated multiple large pulses (which correspond to stents with a reflection image) may be removed; edge points with clustered multiple pulses (which correspond to the boundary of soft tissue and the stent(s)) may be removed; etc.), the gaps in the lumen edge may be filled using simple interpolation (e.g., linear interpolation) using the neighboring edge points. One embodiment example for doing this is to have the lumen edge undergo median filtering.

In one or more method embodiments, a lumen edge may be smoothed (see step S308) of FIG. 8A. For example, the lumen edge may undergo low pass filtering. In one or more embodiments, some simple median filtering and low pass filtering may be applied to lumen edge (edge locations vs. A-line pixels) to smooth and polish the final lumen edge.

In one or more method embodiments, a lumen edge may be converted into Cartesian coordinates (see step S309) of FIG. 8A.

At least one embodiment of a method for detecting lumen edges and artifacts may be summarized as follows: The OCT image in polar coordinates may be filtered using a two dimensional Gaussian filter to reduce the noise in the image. The separate gradient in vertical and horizontal directions may be computed using the Sobel filters from the filtered image. For each A-line, one dimensional filtering is applied to further smooth the A-line signal and remove the signal offset. The gradient along the A-line direction may be further smoothed using a low pass filter. For each A-line, all the significant pulses in the A-line signal may be found, and the most significant pulse and its position may be determined as the lumen data, based on the detection threshold and the pulse size using either pulse width or area under the pulse. The falling rising gradient ratio for the most significant pulse (lumen data) in each A-line may be computed. The lumen data may be removed, and a gap may be identified if the falling rising gradient ration is larger than the threshold value. The lumen data may be removed, and a gap may be identified if the pulse size is smaller than the threshold pulse size. The lumen data may be removed, and a gap may be identified if the detected pulses are multi-peak pulse(s) or where an artifact region detected from the previous step is bordered by the rising and falling peaks of the gradient across A-lines. The lumen data may be removed, and a gap may be identified if there is more than one comparable pulse in the A-line signal. Thereafter, the gaps are filled in the lumen edge using linear interpolation. Median filtering and/or low pass filtering may be applied to the lumen edge. The lumen edge may be converted into Cartesian coordinates for display.

Figure 8B:
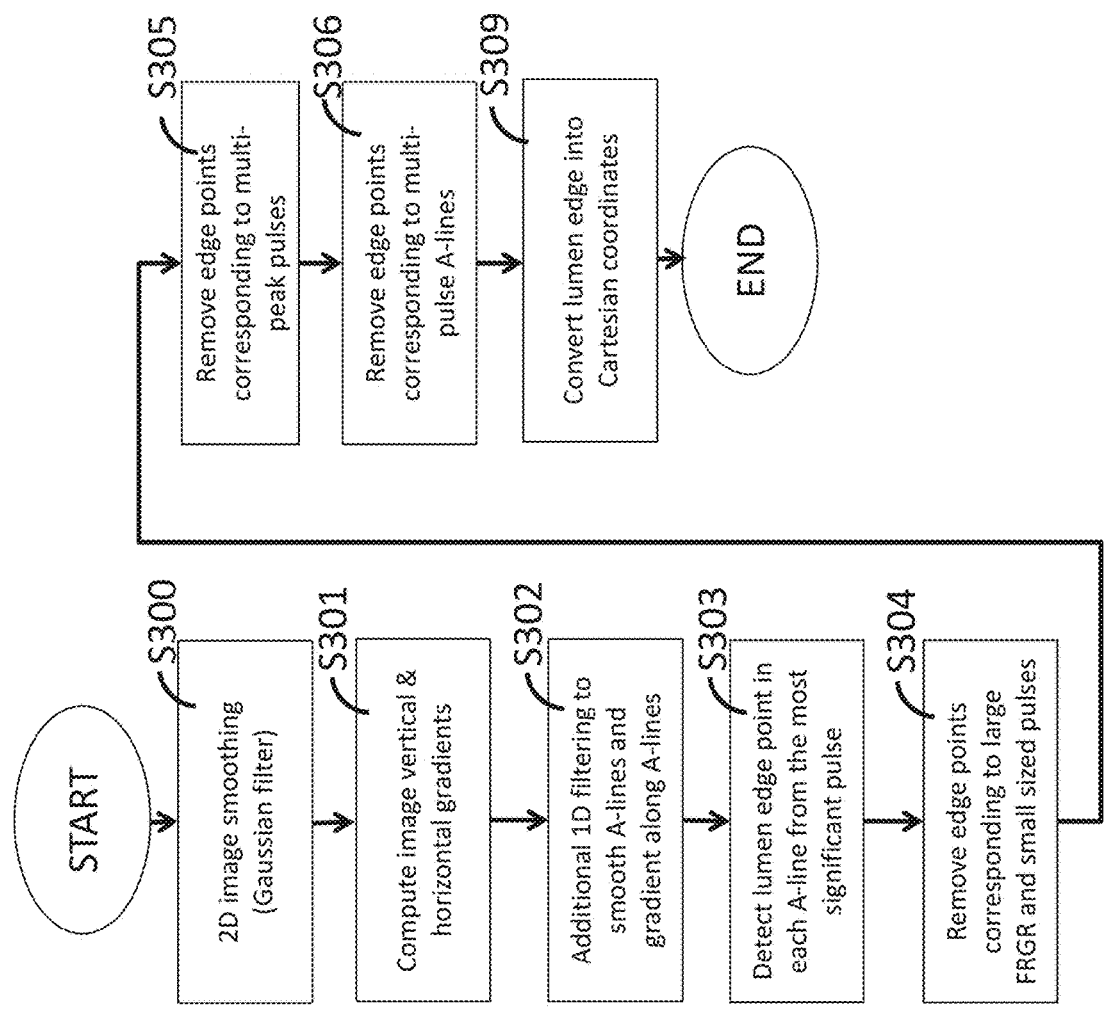

One or more embodiments of a method(s) for detecting lumen and artifacts may be performed with or without the filtering of the lumen edge (e.g., step 307 and/or step 308 of FIG. 8A may be removed as shown in FIG. 8B). For example, median filtering and/or low pass filtering the lumen edge is optional in one or more embodiments. In one or more embodiments, alternative methods for smoothing the lumen edge may be used in place of the median filtering and/or low pass filtering of the lumen edge.

One or more alternative embodiments of a method(s) for detecting lumen and artifacts may be performed by detecting a signal edge pixel from each one-dimensional data (A-line). A-lines with a significant pulse peak may be selected. Each one-dimensional data (A-line) may have its own detection threshold for pulse detection, and the respective threshold may change among different A-lines in an image. A gradient of one-dimensional data (A-line) may be used to further determine the lumen edge pixel location.

One or more alternative embodiments of a method(s) for detecting lumen and artifacts may be performed by introducing an FRGR to distinguish the edges of the target or object (e.g., soft tissue), guide wire(s), stent(s) and/or any other component being used in the procedure. The pulse size of the one dimension data is introduced to distinguish the target or object (e.g., soft tissue), guide wire(s), stent(s), and/or any other component or artifact(s) related to the procedure(s).

One or more alternative embodiments of a method(s) for detecting lumen and artifacts may be performed by identifying the boundary region between the target or object (e.g., soft tissue) and the stent strut(s), guide wire(s), or other artifacts. Multiple peaks in an A-line may represent a blurred boundary between the target or object (e.g., soft tissue) and the stent strut(s), guide wire(s), or other artifacts. The multi-peaks may be used as a signature to identify the boundary.

One or more alternative embodiments of a method(s) for detecting lumen and artifacts may be performed by identifying the boundary region between the target or object (e.g., soft tissue) and narrow stent strut(s). Variation of the gradient along the horizontal direction (across the A-lines) in the region behind the detected lumen edge may be utilized to improve the determination of the location of the artifact region.

One or more alternative embodiments of a method(s) for detecting lumen and artifacts may be performed by identifying ghost signal(s) produced from reflection of stent(s). A ghost signal may cause multiple peaks in an A-line signal. One way to handle this is to remove the area where the multiple pulses/peaks are detected.

As aforementioned for one or more embodiments of a method(s) for detecting lumen and artifacts, interpolation may be used to sample the data that is removed, and to form the lumen edge. The final edge may be smoothed or polished using filters as aforementioned.

A computer, such as the console or computer 1200, 1200', may perform any of the aforementioned steps (e.g., steps S200-S212 of FIG. 3; steps S300-S309 of FIG. 8A; steps S300-S306 and S309 of FIG. 8B; etc.) for any system being manufactured or used, including, but not limited to, system 100, system 100', system 100", system 100''', etc.

Figure 9:
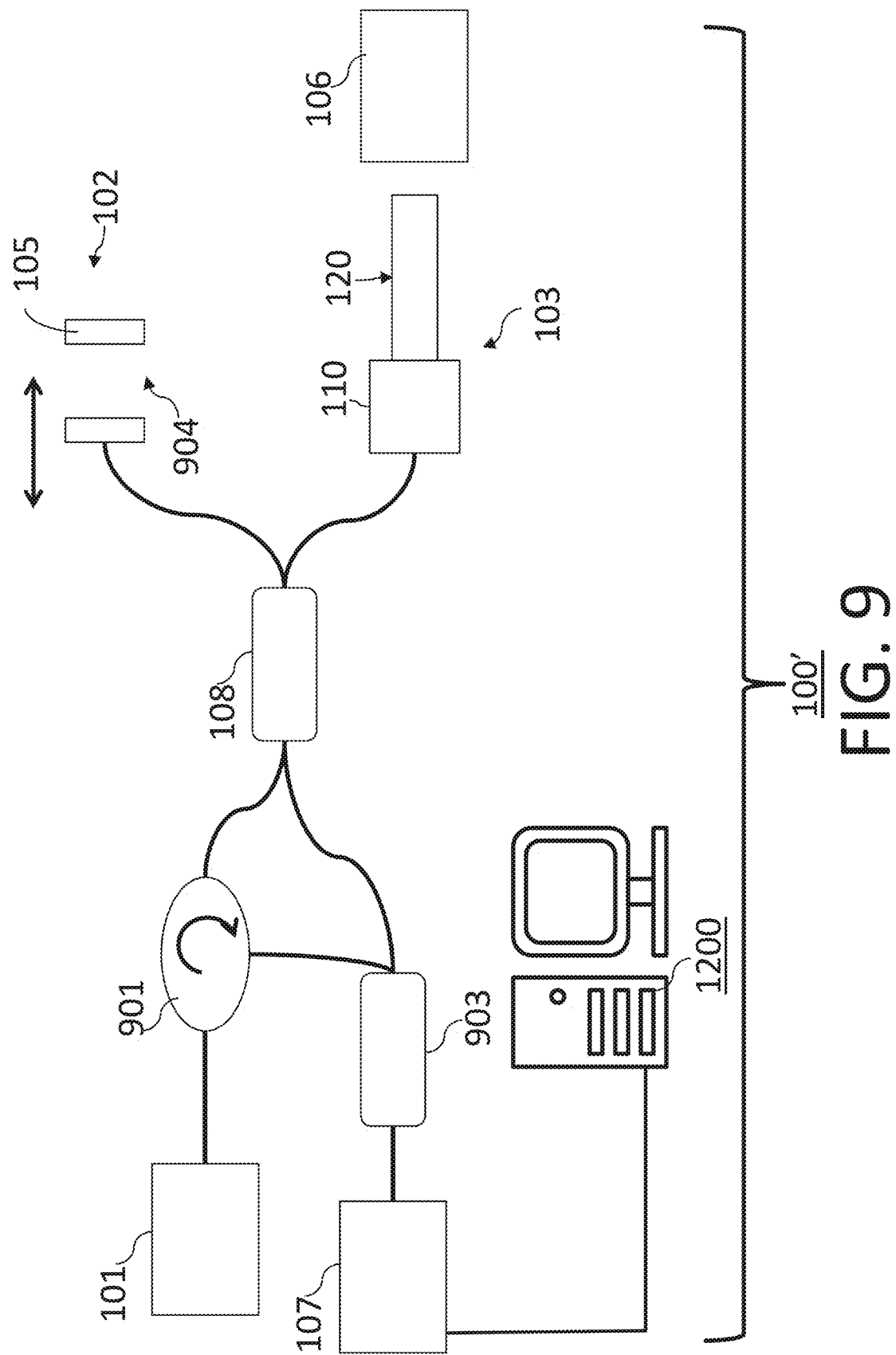
FIG. 9 is a diagram showing an embodiment of at least a second system which can utilize one or more lumen edges, stents, and/or artifacts detection techniques in accordance with one or more aspects of the present disclosure.

In accordance with one or more further aspects of the present disclosure, bench top systems may be utilized with the lumen edge, stent(s), and artifact(s) detection OCT techniques disclosed herein. FIG. 9 shows an example of a system that can utilize the lumen edge and artifact(s) detection OCT techniques for a bench-top such as for ophthalmic applications. A light from a light source 101 delivers and splits into a reference arm 102 and a sample arm 103 with a deflecting (or deflection) section 108. A reference beam goes through a length adjustment section 904 (which is optional in one or more embodiments) and is reflected from a reference mirror (such as reference mirror or reference reflection 105 shown in FIG. 1) in the reference arm 102 while a sample beam is reflected or scattered from a sample, target or object 106 in the sample arm 103 (e.g., via the PIU no and the catheter 120). In one embodiment, both beams combine at the deflecting/deflection section 108 and generate interference patterns. In one or more embodiments, the beams go to the combiner 903, and the combiner 903 combines both beams via the circulator 901 and the deflecting section 108. The combined beams preferably are delivered to one or more detectors (such as the one or more detectors 107). The output of the beam splitter (see e.g., beam splitter 104 in FIG. 1), the deflecting section 108, and/or an interferometer is continuously acquired with one or more detectors, such as the one or more detectors 107. The electrical analog signals are converted to the digital signals to analyze them with a computer, such as, but not limited to, the computer 1200 (see FIG. 1; also shown in FIGS. 9-11 and 12 discussed further below), the computer 1200' (see e.g., FIG. 13 discussed further below), etc.

Figure 10:
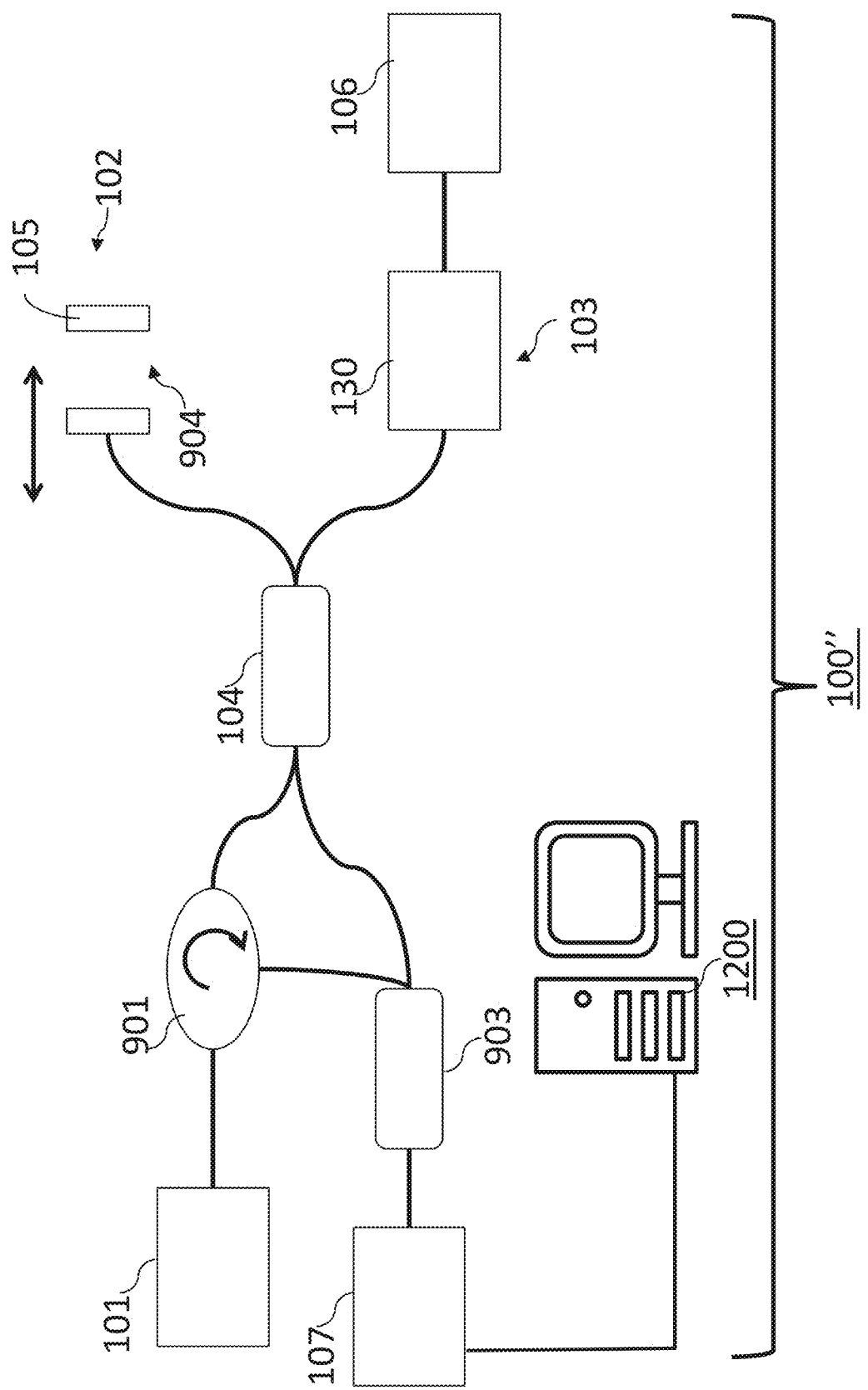
FIG. 10 is a diagram showing an embodiment of at least a third system which can utilize one or more lumen edges, stents, and/or artifacts detection techniques in accordance with one or more aspects of the present disclosure.

In one or more embodiments, the sample arm 103 may include a phase shift unit 103 for a bench top system(s) as shown in system 100" in FIG. 10. The sample 106 may be located at the place of the mirror 105 used with the phase shift unit 130 (e.g., as shown in FIG. 1). A light from a light source 101 delivers and splits into a reference arm 102 and a sample arm 103 with a splitter 104. A reference beam goes through a length adjustment section 904 and is reflected from a reference mirror (such as reference mirror 105 shown in FIGS. 9-11) in the reference arm 102 while a sample beam is reflected or scattered from a sample, target and/or object 106 through a phase shift unit (such as the phase shift unit 130) in the sample arm 103. In one embodiment, both beams combine at the splitter 104 and generate interference patterns. In one or more embodiments, the beams go to the combiner 903, and the combiner 903 combines both beams via the circulator 901 and the splitter 104, and the combined beams are delivered to one or more detectors (such as the one or more detectors 107). The output of the beam splitter 104 and/or an interferometer is continuously acquired with one or more detectors, such as the one or more detectors 107. The electrical analog signals are converted to the digital signals to analyze them with a computer.

There are many ways to compute rotation, intensity, or any other measurement discussed herein, and/or to control and/or manufacture an MMOCT device/apparatus, system and/or storage medium, digital as well as analog. In at least one embodiment, a computer, such as the console or computer 1200, 1200', may be dedicated to control and/or use OCT devices, systems, methods and/or storage mediums for use therewith described herein.

Figure 11:
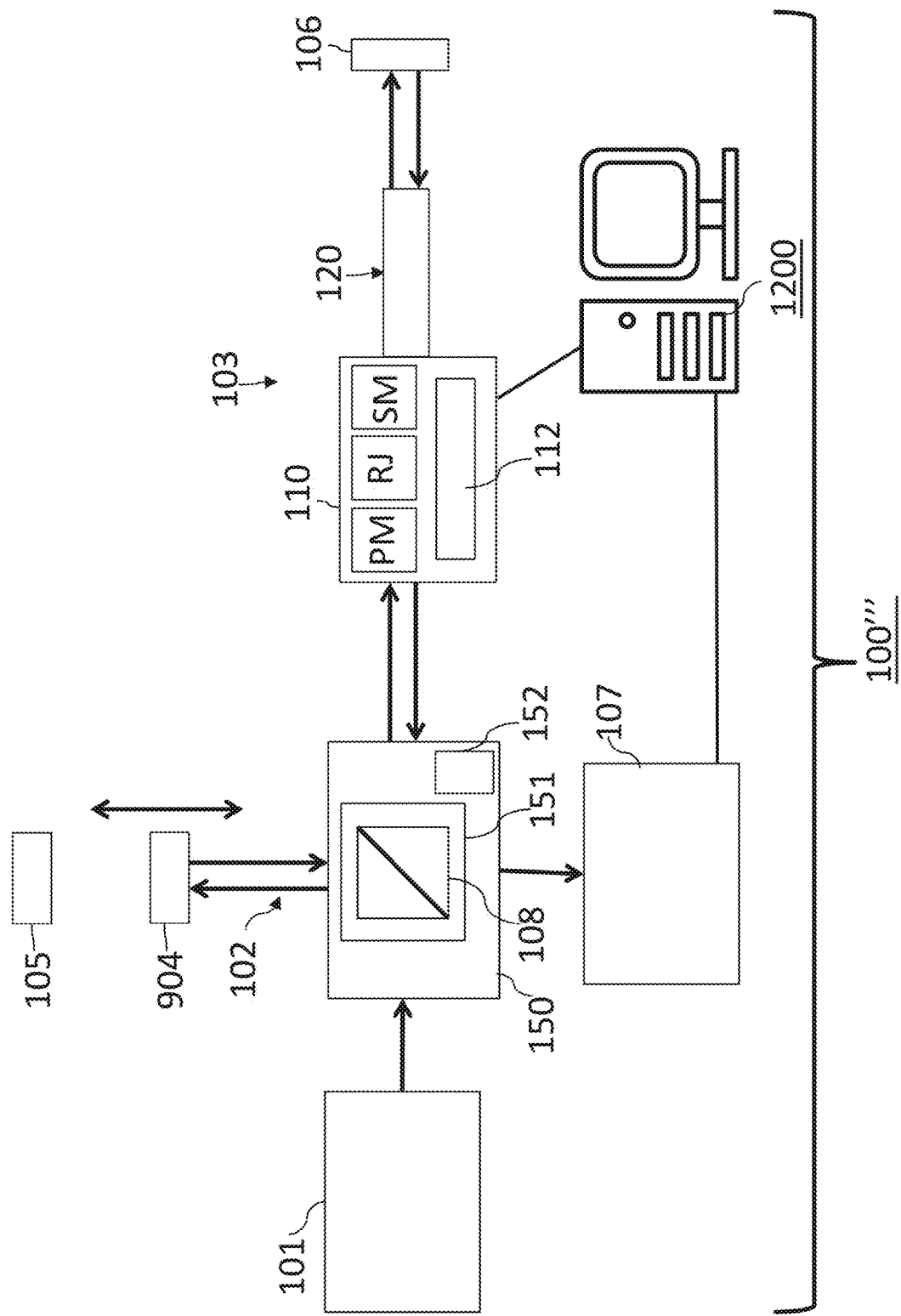
FIG. 11 is a diagram showing an embodiment of at least a fourth system which can utilize one or more lumen edges, stents, and/or artifacts detection techniques in accordance with one or more aspects of the present disclosure.

In accordance with one or more further aspects of the present disclosure, one or more other systems may be utilized with the lumen edge and artifact(s) detection OCT techniques disclosed herein. FIG. 11 shows an example of a system 100''' that may utilize the lumen edge, stent(s), and artifact(s) detection OCT techniques such as for ophthalmic applications. A light from a light source 101 delivers and splits into a reference arm 102 and a sample arm 103 with a deflecting section 108 (e.g., a beam splitter or other deflecting or deflected section discussed herein) located inside of an OCT imaging engine iso, which may also include an OCT interferometer 151 (which may house or include the deflecting section 108) and a swept source engine 152 in one or more embodiments. A reference beam may pass through a length adjustment section 904, which may operate to change the distance of a reference mirror (such as reference mirror or reference reflection 105; also shown in FIG. 1) and is reflected from the reference reflection 105 in the reference arm 102 while a sample beam is reflected or scattered from a sample, target or object 106 in the sample arm 103. In one embodiment, both beams combine at the deflecting section 108 and generate interference patterns. In one or more embodiments, the combined beams are delivered to one or more detectors. The output of the interferometer 151 is continuously acquired with one or more detectors, such as the one or more detectors 107. The electrical analog signals are converted to the digital signals to analyze them with a computer, such as, but not limited to, the computer 1200 (see e.g., FIG. 1; also shown in FIGS. 9-12 discussed further below), the computer 1200' (see e.g., FIG. 13 discussed further below), etc. In one or more embodiments, the sample arm 103 includes the PIU no and the catheter 120 so that the sample beam is reflected or scattered from the sample, target or object 106 as discussed herein. In one or more embodiments, the PIU no may include one or more motors to control the pullback operation of the catheter 120 (or one or more components thereof) and/or to control the rotation or spin of the catheter 120 (or one or more components thereof). For example, the PIU no may include a pullback motor (PM) and a spin motor (SM), and/or may include a motion control unit 112 that operates to perform the pullback and/or rotation features using the pullback motor PM and/or the spin motor SM. As discussed herein, the PIU 110 may include a rotary junction (e.g., rotary junction RJ as shown in FIG. 1*i*). The rotary junction RJ may be connected to the spin motor SM so that the catheter 120 may obtain one or more views or images of the sample 106. The computer 1200 (or the computer 1200') may be used to control one or more of the pullback motor PM, the spin motor SM and/or the motion control unit 112. An OCT system may include one or more of the OCT engine 150, a computer (e.g., the computer 1200, the computer 1200', etc.), the PIU 110, the catheter 120, a monitor, etc. One or more embodiments of an OCT system may interact with one or more external systems, such as, but not limited to, an angio system, external displays, one or more hospital networks, external storage media, a power supply, a bedside controller (e.g., which may be connected to the OCT system using Bluetooth technology or other methods known for wireless communication), etc.

Unless otherwise discussed herein, like numerals indicate like elements. For example, while variations or differences exist between the systems, such as, but not limited to, the system 100, the system 100', the system 100", the system 100''', etc. (e.g., differences between the position(s) of the reference reflection 105 (and/or reference arm 102) depending on the OCT system or method being used), one or more features thereof may be the same or similar to each other, such as, but not limited to, the light source 101, the deflecting section 108 or other component(s) thereof (e.g., the console 1200, the console 1200', etc.). Those skilled in the art will appreciate that the light source 101, the at least one detector 107 and/or one or more other elements of the system 100, may operate in the same or similar fashion to those like-numbered elements of one or more other systems, such as, but not limited to, the system 100', the system 100", the system 100''', etc. as discussed herein. Those skilled in the art will appreciate that alternative embodiments of the system 100, the system 100', the system 100", the system 100''', and/or one or more like-numbered elements of one of such systems, while having other variations as discussed herein, may operate in the same or similar fashion to the like-numbered elements of any of the other systems (or component(s) thereof) discussed herein. Indeed, while certain differences exist between the system 100, the system 100', the system 100" and the system 100''', as discussed herein, there are similarities between the systems discussed herein. Likewise, while the console or computer 1200 may be used in one or more systems (e.g., the system 100, the system 100', the system 100", the system 100''', etc.), one or more other consoles or computers, such as the console or computer 1200', may be used additionally or alternatively.

There are many ways to compute power and/or detect lumen edge(s) and artifact(s), digital as well as analog. In at least one embodiment, a computer, such as the console or computer 1200, 1200', may be dedicated to the control and the monitoring of the OCT devices, systems, methods and/or storage mediums described herein.

The electric signals used for imaging may be sent to one or more processors, such as, but not limited to, a computer 1200 (see e.g., FIGS. 1 and 9-12), a computer 1200' (see e.g., FIG. 13), etc. as discussed further below, via cable(s) or wire(s), such as, but not limited to, the cable(s) or wire(s) 113 (see FIG. 12).

Various components of a computer system 1200 (see e.g., the console or computer 1200 as shown in FIGS. 1 and 9-11) are provided in FIG. 12. A computer system 1200 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS or other connection lines (e.g., connection line 1213) between one or more of the aforementioned components (e.g., as shown in FIG. 12). In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more aforementioned components of a FORJ or a device or system using same, such as, but not limited to, the system 100, the system 100', the system 100" and/or the system 100'", discussed herein above, via one or more lines 1213), and one or more other computer systems 1200 may include one or more combinations of the other aforementioned components. The CPU 1201 is configured to read and perform computer-executable instructions stored in a storage medium. The computer-executable instructions may include those for the performance of the methods and/or calculations described herein. The computer system 1200 may include one or more additional processors in addition to CPU 1201, and such processors, including the CPU 1201, may be used for controlling and/or manufacturing a device, system or storage medium for use with same or for use with any lumen detection, stent(s) detection, and/or artifact(s) detection technique(s) discussed herein. The system 1200 may further include one or more processors connected via a network connection (e.g., via network 1206). The CPU 1201 and any additional processor being used by the system 1200 may be located in the same telecom network or in different telecom networks (e.g., performing, manufacturing, controlling and/or using technique(s) may be controlled remotely).

The I/O or communication interface 1205 provides communication interfaces to input and output devices, which may include the light source 101, a RJ, a PM, an SM, unit 150, unit 112, a microphone, a communication cable and a network (either wired or wireless), a keyboard 1210, a mouse (see e.g., the mouse 1211 as shown in FIG. 13), a touch screen or screen 1209, a light pen and so on. The Monitor interface or screen 1209 provides communication interfaces thereto.

Any methods and/or data of the present disclosure, such as the methods for using and/or manufacturing a device, system or storage medium for use with same and/or method(s) for detecting lumen edge(s), stent(s), and/or artifact(s), including in OCT image(s), as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 13), SRAM, etc.), an optional combination thereof, a server/database, etc. may be used to cause a processor, such as, the processor or CPU 1201 of the aforementioned computer system 1200 to perform the steps of the methods disclosed herein. The computer-readable storage medium may be a non-transitory computer-readable medium, and/or the computer-readable medium may comprise all computer-readable media, with the sole exception being a transitory, propagating signal. The computer-readable storage medium may include media that store information for predetermined, limited, or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, devices, systems, and computer-readable storage mediums related to the processors, such as, but not limited to, the processor of the aforementioned computer 1200, the processor of computer 1200', etc., as described above may be achieved utilizing suitable hardware, such as that illustrated in the figures. Functionality of one or more aspects of the present disclosure may be achieved utilizing suitable hardware, such as that illustrated in FIG. 12. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 12 or FIG. 13) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium.

As aforementioned, hardware structure of an alternative embodiment of a computer or console 1200' is shown in FIG. 13. The computer 1200' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid-state drive (SSD) 1207. Preferably, the computer or console 1200' includes a display 1209. The computer 1200' may connect with a rotary junction (e.g., RJ of FIG. 11, etc.), the motor PM, the motor SM, and/or one or more other components of a system (e.g., the system 100, the system 100', the system 100", the system 100''', etc.) via the operation interface 1214 or the network interface 1212. A computer, such as the computer 1200, 1200', may include the RJ, PM and/or the SM in one or more embodiments. The operation interface 1214 is connected with an operation unit such as a mouse device 1211, a keyboard 1210 or a touch panel device. The computer 1200' may include two or more of each component. Alternatively, the CPU 1201 or the GPU 1215 may be replaced by the field-programmable gate array (FPGA), the application-specific integrated circuit (ASIC) or other processing unit depending on the design of a computer, such as the computer 1200, the computer 1200', etc.

A computer program is stored in the SSD 1207, and the CPU 1201 loads the program onto the RAM 1203, and executes the instructions in the program to perform one or more processes described herein, as well as the basic input, output, calculation, memory writing and memory reading processes.

The computer, such as the computer 1200, 1200', communicates with the PIU 110, the rotary junction (e.g., the RJ, etc.), the motor PM, the motor SM, the catheter 120 and/or one or more other components of a system, such as the system 100, 100', 100", 100''', etc., to perform imaging, and reconstructs an image from the acquired intensity data. The monitor or display 1209 displays the reconstructed image, and may display other information about the imaging condition or about an object to be imaged. The monitor 1209 also provides a graphical user interface for a user to operate a system (e.g., the system 100, the system 100', the system 100", the system 100''', etc.), for example when performing OCT or other imaging technique, including, but not limited to, detection of lumen edge(s) and/or artifact(s). An operation signal is input from the operation unit (e.g., such as, but not limited to, a mouse device 1211, a keyboard 1210, a touch panel device, etc.) into the operation interface 1214 in the computer 1200', and corresponding to the operation signal the computer 1200' instructs the system (e.g., the system 100, the system 100', the system 100", the system 100''', etc.) to set or change the imaging condition, and to start or end the imaging, and/or to start or end the lumen detection, stent(s) detection, and/or artifact(s) detection. The laser source 101 of an OCT system as aforementioned may have interfaces to communicate with the computers 1200, 1200' to send and receive the status information and the control signals.

Similarly, the present disclosure and/or one or more components of devices, systems and storage mediums, and/or methods, thereof also may be used in conjunction with optical coherence tomography probes. Such probes include, but are not limited to, the OCT imaging systems disclosed in U.S. Pat. Nos. 7,872,759; 8,289,522; and U.S. Pat. No. 8,928,889 to Tearney et al. and arrangements and methods of facilitating photoluminescence imaging, such as those disclosed in U.S. Pat. No. 7,889,348 to Tearney et al., as well as the disclosures directed to multimodality imaging disclosed in U.S. Pat. No. 9,332,942 and U.S. Patent Publication Nos. 2010/0092389, 2012/0101374, 2016/0228097, 2018/0045501 and 2018/0003481, each of which patents, patent publications and patent application(s) are incorporated by reference herein in their entireties. As aforementioned, any feature or aspect of the present disclosure may be used with OCT imaging systems, apparatuses, methods, storage mediums or other aspects or features as discussed in U.S. patent application Ser. No. 16/414,222, filed on May 16, 2019 and published on Dec. 12, 2019 as U.S. Pat. Pub. No. 2019/0374109, the entire disclosure of which is incorporated by reference herein in its entirety.

Although the disclosure herein has been described with reference to particular embodiments, it is to be understood that these embodiments are merely illustrative of the principles and applications of the present disclosure (and are not limited thereto). It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications and equivalent structures and functions.

The invention claimed is:

1. An optical coherence tomography ("OCT") system for detecting one or more lumen edges and for detecting one or more stents or stent struts and/or one or more artifacts in one or more images, the system comprising:
   one or more processors that operate to:
   use filtered OCT polar coordinate image data to detect one or more of the lumen edges, one or more stents or stent struts, and/or one or more artifacts in the one or more images;
   detect and exclude or remove a sheath from the OCT polar coordinate image data;
   find a major peak and edge in each one-dimensional (1D) data or A-line of the OCT polar coordinate image data, and use the major peak and edge to at least determine whether the major peak and edge correspond to a valid lumen edge of the one or more of the lumen edges using a local lumen edge threshold for a specific 1D data or A-line of the OCT polar coordinate image data, wherein the major peak is the maximum peak or a most significant pulse, and, in a case where the major peak and edge are confirmed to correspond to a valid lumen edge of the one or more of the lumen edges using the local lumen edge threshold and where a plurality of major peaks and edges are confirmed to correspond to one or more valid lumen edges using a respective local lumen edge threshold for each 1D data or A-line of the OCT polar coordinate image data corresponding to one or more of the plurality of major peaks and edges, identify a plurality of lumen edge points for the 1D data or for the OCT polar coordinate image data, and combine the plurality of lumen edge points to form and/or estimate the one or more valid lumen edges;
   detect and remove a guide wire;

detect and process one or more stent candidates based on the major peak;

merge and extend a stent region;

calculate a shadow profile and find or confirm the stent or stent strut and/or a center of the stent or stent strut;

extract a lumen edge or edges or portions of the lumen edge or edges near a border of the lumen and the one or more stents or stent struts;

interpolate missing data or one or more parts of the extracted lumen edge or edges or of the extracted portions of the lumen edge or edges to form an additional valid lumen edge or edges and combine the additional valid lumen edge or edges with the formed and/or estimated one or more valid lumen edges to create a whole lumen curve;

find one or more embedded stents or stent struts using the whole lumen curve; and output or store the lumen edge or edges and/or the whole lumen curve and output or store stent strut information and/or a location of the center of the stent or stent strut.

2. The system of claim 1, wherein the one or more processors further operate to one or more of the following:

detect one or more peaks and associated edges from the 1D data or the A-line data;

calculate one or more peak widths on the 1D data or the A-line data and a gradient of the 1D data or the A-line data;

accept one or more objects on the same A-line;

group the one or more objects together based on a connectivity between neighbor A-lines; and distinguish different objects based on a peak value, peak and edge positions, and different width values.

3. The system of claim 1, wherein the one or more processors further operate to exclude or remove the sheath and remove the guide wire using one or more characteristics of the sheath and/or guide wire to improve a success rate of detecting the lumen edge and the one or more stents or stent struts.

4. The system of claim 1, wherein the one or more processors further operate to detect the stent candidates using an edge position jump and a narrow peak width pattern.

5. The system of claim 1, wherein the one or more processors further operate to process each of the one or more stent candidates at a local region and search neighbor lumen edges on both sides of the guide wire and/or the one or more stent strut(s).

6. The system of claim 1, wherein the one or more processors further operate to use the interpolation of the lumen edge to calculate the shadow profile, to confirm or find a shadow of the one or more stents or stent struts, and/or to confirm or find the center location of the one or more stents or stent struts.

7. The system of claim 1, wherein the one or more processors further operate to one or more of the following:

perform the extraction of the lumen edge(s) or the portions of the lumen edge(s) from secondary peaks near the border of the lumen and the one or more stents or stent struts, the extracted lumen edge(s) or portions of the lumen edges being used to form the additional valid lumen edge or edges;

identify one or more valid lumen edges or portions of the lumen edge or edges that exist as secondary peaks behind a stent peak near the border region; and/or include the extracted one or more valid lumen edges in lumen edge results to improve the quality of the lumen edge results and to help form or create the whole lumen curve.

8. The system of claim 7, wherein the extraction of the lumen edge(s) or the portions of the lumen edge(s) are based on a connectivity of the current lumen edge or edges by searching a secondary peak of the secondary peaks outside of the major peak on the A-line that already has been identified or that is identified as a non-lumen peak, and/or wherein the extraction process searches on both sides of the one or more stents or stent struts until no further peak is found.

9. The system of claim 1, wherein the one or more processors further operate to one or more of the following:

interpolate both missing portions of the lumen edge or edges or the missing lumen edge or edges and the lumen peak to form complete enclosing curves of the lumen edge or edges for the whole lumen curve; and/or calculate the shadow profile based on a profile of the interpolated peaks to identify the embedded stent region, and search the stent or stent strut using a peak width pattern.

10. The system of claim 1, wherein the one or more processors further operate to one or more of the following:

detect the one or more of the lumen edges, the guide wire, the one or more stents or stent struts, and/or one or more other artifacts in polar coordinate images or the polar coordinate image data, based on the information on each A-line, and then using neighbor A-line information to group or classify the detected one or more of the lumen edges, the detected guide wire, the detected one or more stents or stent struts, and/or the detected one or more other artifacts into objects or object types;

extract the objects from the polar coordinate images in such a manner that levels of layers are identified and a next level of results has a lesser or smaller region of interest to work with and has a confidence or additional confidence of the grouped or classified objects or object types; and/or performing processing in, or adopting, an iterative manner to add information on extracted objects on each A-line, and to fully cover all A-lines and objects that can be detected in the polar coordinate images.

11. The system of claim 1, further comprising one or more of the following:

a light source that operates to produce a light;

an interference optical system that operates to: (i) receive and divide the light from the light source into a first light with which an object or sample is to be irradiated and a second reference light, (ii) send the second reference light for reflection off of a reference mirror of the interference optical system, and (iii) generate interference light by causing reflected or scattered light of the first light with which the object or sample has been irradiated and the reflected second reference light to combine or recombine, and to interfere, with each other, the interference light generating one or more interference patterns; and/or one or more detectors that operate to continuously acquire the interference light and/or the one or more interference patterns such that the one or more lumen edges, the one or more stents, and/or the one or more artifacts are detected in the images, and the one or more stents and/or the one or more artifacts are removed from the one or more images.

12. A method for detecting one or more lumen edges and for detecting one or more stents or stent struts and/or one or more artifacts in at least one image, the method comprising:
  using filtered optical coherence tomography ("OCT") polar coordinate image data to detect one or more of the lumen edges, one or more stents or stent struts, and/or one or more artifacts in the one or more images;
  detecting and excluding or removing a sheath from the OCT polar coordinate image data;
  finding a major peak and edge in each one-dimensional (1D) data or A-line of the OCT polar coordinate image data, and using the major peak and edge to at least determine whether the major peak and edge correspond to a valid lumen edge of the one or more of the lumen edges using a local lumen edge threshold for the specific 1D data or A-line of the OCT polar coordinate image data, wherein the major peak is the maximum peak or a most significant pulse, and, in a case where the major peak and edge are confirmed to correspond to a valid lumen edge of the one or more of the lumen edges using the local lumen edge threshold and where a plurality of major peaks and edges are confirmed to correspond to one or more valid lumen edges using a respective local lumen edge threshold for each 1D data or A-line of the OCT polar coordinate image data corresponding to one or more of the plurality of major peaks and edges, identify a plurality of lumen edge points for the 1D data or for the OCT polar coordinate image data, and combine the plurality of lumen edge points to form and/or estimate the one or more valid lumen edges;
  detecting and removing a guide wire;
  detecting and processing one or more stent candidates based on the major peak;
  merging and extending a stent region;
  calculating a shadow profile and finding or confirming the stent or stent strut and/or a center of the stent or stent strut;
  extracting a lumen edge or edges or portions of the lumen edge or edges near a border of the lumen and the one or more stents or stent struts;
  interpolating missing data or one or more parts of the extracted lumen edge or edges or of the extracted portions of the lumen edge or edges to form an additional valid lumen edge or edges and combine the additional valid lumen edge or edges with the formed and/or estimated one or more valid lumen edges to create a whole lumen curve;
  finding one or more embedded stents or stent struts using the whole lumen curve; and
  outputting or storing the lumen edge or edges and/or the whole lumen curve and outputting or storing stent strut information and/or a location of the center of the stent or stent strut.

13. The method of claim 12, further comprising one or more of the following:
  detecting one or more peaks and associated edges from the 1D data or the A-line data;
  calculating one or more peak widths on the 1D data or the A-line data and a gradient of the 1D data or the A-line data;
  accepting one or more objects on the same A-line;
  grouping the one or more objects together based on a connectivity between neighbor A-lines; and
  distinguishing different objects based on a peak value, peak and edge positions, and different width values.

14. The method of claim 12, wherein the exclusion or removal of the sheath and the removal of the guide wire includes using one or more characteristics of the sheath and/or guide wire to improve a success rate of detecting the lumen edge and the one or more stents or stent struts.

15. The method of claim 12, wherein the detection of the stent candidates includes using an edge position jump and a narrow peak width pattern.

16. The method of claim 12, wherein the processing of the one or more stent candidates includes processing each of the one or more stent candidates at a local region and searching neighbor lumen edges on both sides of the guide wire and/or the one or more stent strut(s).

17. The method of claim 12, wherein the interpolation of the lumen edge is used to calculate the shadow profile, to confirm or find a shadow of the one or more stents or stent struts, and/or to confirm or find the center location of the one or more stents or stent struts.

18. The method of claim 12, further comprising one or more of the following:
  performing the extracting of the lumen edge(s) or the portions of the lumen edge(s) from secondary peaks near the border of the lumen and the one or more stents or stent struts, the extracted lumen edge(s) or portions of the lumen edges being used to form the additional valid lumen edge or edges;
  identifying one or more valid lumen edges or portions of the lumen edge or edges that exist as the second peaks behind a stent peak near the border region; and/or
  including the extracted one or more valid lumen edges in lumen edge results to improve the quality of the lumen edge results and to help form or create the whole lumen curve.

19. The method of claim 18, wherein the extraction of the lumen edge(s) or the portions of the lumen edge(s) are based on a connectivity of the current lumen edge or edges by searching a secondary peak of the secondary peaks outside of the major peak on the A-line that already has been identified or that is identified as a non-lumen peak, and/or wherein the extraction process searches on both sides of the one or more stents or stent struts until no further peak is found.

20. The method of claim 12, wherein one or more of the following:
  the interpolation of the missing data or the one or more portions of the extracted lumen edge or edges includes interpolating both missing portions of the extracted lumen edge or edges or the missing lumen edge or edges and the lumen peak to form complete enclosing curves of the lumen edge or edges for the whole lumen curve; and/or
  the calculation of the shadow profile or shadow accumulation profile includes calculating the shadow profile based on a profile of the interpolated peaks to identify the embedded stent region, and searching the stent or stent strut using a peak width pattern.

21. The method of claim 12, further comprises one or more of the following:
  detecting the one or more of the lumen edges, the guide wire, the one or more stents or stent struts, and/or one or more other artifacts in polar coordinate images or the polar coordinate image data, based on the information on each A-line, and then using neighbor A-line information to group or classify the detected one or more of the lumen edges, the detected guide wire, the detected one or more stents or stent struts, and/or the detected one or more other artifacts into objects or object types;

extracting the objects from the polar coordinate images in such a manner that levels of layers are identified and a next level of results has a lesser or smaller region of interest to work with and has a confidence or additional confidence of the grouped or classified objects or object types; and/or performing processing in, or adopting, an iterative manner to add information on extracted objects on each A-line, and to fully cover all A-lines and objects that can be detected in the polar coordinate images.

22. The method of claim 12, wherein one or more of:

a target or object being image in the at least one image is one or more of: tissue, soft tissue, a vessel, a biological tubular structure, an artery, an intestine, a vein, an organ, and/or a biological structure of a patient being imaged; and the one or more artifacts includes one or more of: a stent, a stent strut, stents, stent struts, a guidewire, guidewires, and/or any tool or component used for an imaging procedure for the at least one image.

23. A non-transitory computer-readable storage medium storing at least one program that operates to cause one or more processors to execute a method for detecting one or more lumen edges and for detecting one or more stents or stent struts and/or one or more artifacts in at least one image, the method comprising:

using filtered optical coherence tomography ("OCT") polar coordinate image data to detect one or more of the lumen edges, one or more stents or stent struts, and/or one or more artifacts in the one or more images;

detecting and excluding or removing a sheath from the OCT polar coordinate image data;

finding a major peak and edge in each one-dimensional (1D) data or A-line of the OCT polar coordinate image data, and using the major peak and edge to at least determine whether the major peak and edge correspond to a valid lumen edge of the one or more of the lumen edges using a local lumen edge threshold for the specific 1D data or A-line of the OCT polar coordinate image data, wherein the major peak is the maximum peak or a most significant pulse, and, in a case where the major peak and edge are confirmed to correspond to a valid lumen edge of the one or more of the lumen edges using the local lumen edge threshold and where a plurality of major peaks and edges are confirmed to correspond to one or more valid lumen edges using a respective local lumen edge threshold for each 1D data or A-line of the OCT polar coordinate image data corresponding to one or more of the plurality of major peaks and edges, identify a plurality of lumen edge points for the 1D data or for the OCT polar coordinate image data, and combine the plurality of lumen edge points to form and/or estimate the one or more valid lumen edges;

detecting and removing a guide wire;

detecting and processing one or more stent candidates based on the major peak;

merging and extending a stent region;

calculating a shadow profile and finding or confirming the stent or stent strut and/or a center of the stent or stent strut;

extracting a lumen edge or edges or portions of the lumen edge or edges near a border of the lumen and the one or more stents or stent struts;

interpolating missing data or one or more parts of the extracted lumen edge or edges or of the extracted portions of the lumen edge or edges to form an additional valid lumen edge or edges and combine the additional valid lumen edge or edges with the formed and/or estimated one or more valid lumen edges to create a whole lumen curve;

finding one or more embedded stents or stent struts using the whole lumen curve; and outputting or storing the lumen edge or edges and/or the whole lumen curve and outputting or storing stent strut information and/or a location of the center of the stent or stent strut.

\* \* \* \* \*